(12) United States Patent
Cornelussen et al.

(10) Patent No.: US 8,781,583 B2
(45) Date of Patent: Jul. 15, 2014

(54) VAGAL STIMULATION

(75) Inventors: Richard N. M. Cornelussen, Maastricht (NL); Xiaohong Zhou, Woodbury, MN (US); Robert Stadler, Minnesota, MN (US); Lilian Kornet, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/353,919

(22) Filed: Jan. 19, 2012

(65) Prior Publication Data

US 2012/0185011 A1    Jul. 19, 2012

Related U.S. Application Data

(60) Provisional application No. 61/434,279, filed on Jan. 19, 2011.

(51) Int. Cl.
*A61N 1/36* (2006.01)
(52) U.S. Cl.
USPC .......................................................... 607/18
(58) Field of Classification Search
None
See application file for complete search history.

(56) References Cited

U.S. PATENT DOCUMENTS

| | | | |
|---|---|---|---|
| 3,674,013 A | 7/1972 | Polanyl | |
| 3,804,098 A | 4/1974 | Friedman | |
| 3,937,226 A | 2/1976 | Funke | |
| 4,088,138 A | 5/1978 | Diack et al. | |
| 4,088,140 A | 5/1978 | Rockland et al. | |
| 4,161,952 A | 7/1979 | Kinney et al. | |
| 4,176,660 A | 12/1979 | Mylrea et al. | |
| 4,198,963 A | 4/1980 | Barkalow et al. | |
| 4,303,075 A | 12/1981 | Heilman et al. | |
| 4,304,239 A | 12/1981 | Perlin | |
| 4,321,929 A | 3/1982 | Lemelson et al. | |
| 4,332,259 A | 6/1982 | McCorkle, Jr. | |
| 4,351,330 A | 9/1982 | Scarberry | |
| 4,354,497 A | 10/1982 | Kahn | |
| 4,428,378 A | 1/1984 | Anderson et al. | |
| 4,458,677 A | 7/1984 | McCorkle, Jr. | |
| 4,485,813 A | 12/1984 | Anderson et al. | |
| 4,535,774 A | 8/1985 | Olson | |
| 4,548,203 A | 10/1985 | Tacker, Jr. et al. | |
| 4,574,807 A | 3/1986 | Hewson et al. | |
| 4,603,705 A | 8/1986 | Speicher et al. | |

(Continued)

FOREIGN PATENT DOCUMENTS

| AU | 199890156 | 3/1999 |
|---|---|---|
| AU | 779255 | 1/2001 |

(Continued)

OTHER PUBLICATIONS

Adams, "Gains in Pain Research: Past Failures Push Investigators to be More Innovative in their Treatment Approaches," *The Scientist*, Dec. 15, 2003; 17(24); 6 pages.

(Continued)

*Primary Examiner* — Carl H Layno
*Assistant Examiner* — Paula J Stice
(74) *Attorney, Agent, or Firm* — Carol F. Barry

(57) ABSTRACT

The disclosure herein relates generally to methods for treating heart conditions using vagal stimulation, and further to systems and devices for performing such treatment. Such methods may include monitoring physiological parameters of a patient, detecting cardiac conditions, and delivering vagal stimulation (e.g., electrical stimulation to the vagus nerve or neurons having parasympathetic function) to the patient to treat the detected cardiac conditions.

14 Claims, 15 Drawing Sheets

(56) References Cited

U.S. PATENT DOCUMENTS

| | | |
|---|---|---|
| 4,640,298 A | 2/1987 | Pless et al. |
| 4,671,295 A | 6/1987 | Abrams et al. |
| 4,715,367 A | 12/1987 | Crossley |
| 4,722,347 A | 2/1988 | Abrams et al. |
| 4,750,495 A | 6/1988 | Moore et al. |
| 4,753,244 A | 6/1988 | Landymore et al. |
| 4,919,147 A | 4/1990 | Reinhardt et al. |
| 4,928,688 A | 5/1990 | Mower |
| 4,929,688 A | 5/1990 | Allen et al. |
| 4,931,464 A | 6/1990 | Grover et al. |
| 4,951,667 A | 8/1990 | Markowitz et al. |
| 4,952,586 A | 8/1990 | Morris et al. |
| 4,960,133 A | 10/1990 | Hewson |
| 4,969,463 A | 11/1990 | Dahl et al. |
| 5,003,991 A | 4/1991 | Takayama et al. |
| 5,007,893 A | 4/1991 | Row |
| 5,014,698 A | 5/1991 | Cohen |
| 5,024,228 A | 6/1991 | Goldstone et al. |
| 5,025,807 A | 6/1991 | Zabara |
| 5,036,848 A | 8/1991 | Hewson |
| 5,044,367 A | 9/1991 | Endres et al. |
| 5,050,600 A | 9/1991 | Parks |
| 5,052,390 A | 10/1991 | Hewson |
| 5,056,519 A | 10/1991 | Vince |
| 5,056,532 A | 10/1991 | Hull et al. |
| 5,117,822 A | 6/1992 | Laghi |
| 5,117,828 A | 6/1992 | Metzger et al. |
| 5,125,406 A | 6/1992 | Goldstone et al. |
| 5,127,407 A | 7/1992 | Tan |
| 5,129,392 A | 7/1992 | Bardy et al. |
| 5,154,170 A | 10/1992 | Bennett et al. |
| 5,154,172 A | 10/1992 | Terry, Jr. et al. |
| 5,156,149 A | 10/1992 | Hudrlik |
| 5,156,151 A | 10/1992 | Imran |
| 5,174,289 A | 12/1992 | Cohen |
| 5,178,149 A | 1/1993 | Imburgia et al. |
| 5,179,950 A | 1/1993 | Stanislaw |
| 5,179,952 A | 1/1993 | Buinevicius et al. |
| 5,186,170 A | 2/1993 | Varrichio et al. |
| 5,188,104 A | 2/1993 | Wernicke et al. |
| 5,199,428 A | 4/1993 | Obel et al. |
| 5,203,326 A | 4/1993 | Collins |
| 5,205,285 A | 4/1993 | Baker, Jr. |
| 5,215,086 A | 6/1993 | Terry, Jr. et al. |
| 5,231,988 A | 8/1993 | Wernicke et al. |
| 5,235,980 A | 8/1993 | Varrichio et al. |
| 5,243,980 A | 9/1993 | Mehra |
| 5,263,480 A | 11/1993 | Wernicke et al. |
| 5,265,603 A | 11/1993 | Hudrlik |
| 5,265,623 A | 11/1993 | Kroll et al. |
| 5,267,560 A | 12/1993 | Cohen |
| 5,269,298 A | 12/1993 | Adams et al. |
| 5,269,303 A | 12/1993 | Wernicke et al. |
| 5,282,468 A | 2/1994 | Klepinski |
| 5,284,146 A | 2/1994 | Czar et al. |
| 5,292,338 A | 3/1994 | Bardy |
| 5,299,569 A | 4/1994 | Wernicke et al. |
| 5,304,120 A | 4/1994 | Crandell et al. |
| 5,304,206 A | 4/1994 | Baker, Jr. et al. |
| 5,304,220 A | 4/1994 | Maginot |
| 5,306,293 A | 4/1994 | Zacouto |
| 5,315,995 A | 5/1994 | Rivers |
| 5,320,642 A | 6/1994 | Scherlag |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,354,318 A | 10/1994 | Taepke |
| 5,356,425 A | 10/1994 | Bardy et al. |
| 5,365,926 A | 11/1994 | Desai |
| 5,379,765 A | 1/1995 | Kajiwara et al. |
| 5,403,356 A | 4/1995 | Hill et al. |
| 5,411,529 A | 5/1995 | Hudrlik |
| 5,411,531 A | 5/1995 | Hill et al. |
| 5,417,713 A | 5/1995 | Cohen |
| 5,423,877 A | 6/1995 | Mackey |
| 5,456,254 A | 10/1995 | Pietroski et al. |
| 5,458,625 A | 10/1995 | Kendall |
| 5,476,485 A | 12/1995 | Wienberg et al. |
| 5,501,702 A | 3/1996 | Plicchi et al. |
| 5,501,703 A | 3/1996 | Holsheimer et al. |
| 5,507,784 A | 4/1996 | Hill et al. |
| 5,514,161 A | 5/1996 | Limousin |
| 5,522,853 A | 6/1996 | Kroll |
| 5,522,854 A | 6/1996 | Ideker et al. |
| 5,531,776 A | 7/1996 | Ward et al. |
| 5,540,730 A | 7/1996 | Terry, Jr. |
| 5,540,732 A | 7/1996 | Testerman |
| 5,545,186 A | 8/1996 | Olson et al. |
| 5,549,655 A | 8/1996 | Erickson |
| 5,571,150 A | 11/1996 | Wernicke et al. |
| 5,578,061 A | 11/1996 | Stroetmann et al. |
| 5,584,867 A | 12/1996 | Limousin |
| 5,611,350 A | 3/1997 | John |
| 5,620,468 A | 4/1997 | Mongeon et al. |
| 5,632,267 A | 5/1997 | Hognelid et al. |
| 5,651,378 A | 7/1997 | Matheny et al. |
| 5,656,420 A | 8/1997 | Chien |
| 5,658,318 A | 8/1997 | Stroetmann et al. |
| 5,662,689 A | 9/1997 | Elsberry et al. |
| 5,668,117 A | 9/1997 | Shapiro |
| 5,674,259 A | 10/1997 | Gray |
| 5,683,429 A | 11/1997 | Mehra |
| 5,690,681 A | 11/1997 | Geddes et al. |
| 5,700,282 A | 12/1997 | Zabara |
| 5,707,400 A | 1/1998 | Terry, Jr. et al. |
| 5,713,924 A | 2/1998 | Min et al. |
| 5,713,929 A | 2/1998 | Hess et al. |
| 5,720,768 A | 2/1998 | Verboven-Nelissen |
| 5,755,682 A | 5/1998 | Knudson et al. |
| 5,782,874 A | 7/1998 | Loos |
| 5,791,187 A | 8/1998 | Chang |
| 5,792,187 A | 8/1998 | Adams |
| 5,792,203 A | 8/1998 | Schroeppel |
| 5,797,970 A | 8/1998 | Pouvreau |
| 5,799,661 A | 9/1998 | Boyd et al. |
| 5,824,021 A | 10/1998 | Rise |
| 5,836,994 A | 11/1998 | Bourgeois |
| 5,840,076 A | 11/1998 | Swanson et al. |
| 5,843,133 A | 12/1998 | Routh et al. |
| 5,846,263 A | 12/1998 | Peterson et al. |
| 5,846,264 A | 12/1998 | Andersson et al. |
| 5,855,592 A | 1/1999 | McGee et al. |
| 5,865,838 A | 2/1999 | Obel et al. |
| 5,874,420 A | 2/1999 | Pelleg |
| 5,876,422 A | 3/1999 | van Groeningen |
| 5,889,033 A | 3/1999 | Kaminski |
| 5,893,881 A | 4/1999 | Elsberry et al. |
| 5,893,882 A | 4/1999 | Peterson et al. |
| 5,902,324 A | 5/1999 | Thompson et al. |
| 5,913,876 A | 6/1999 | Taylor et al. |
| 5,916,239 A | 6/1999 | Geddes et al. |
| 5,928,272 A | 7/1999 | Adkins et al. |
| 5,964,789 A | 10/1999 | Karsdon |
| 5,971,911 A | 10/1999 | Wilk |
| 5,977,408 A | 11/1999 | Levin et al. |
| 5,978,700 A | 11/1999 | Nigam |
| 5,991,656 A | 11/1999 | Olson et al. |
| 5,995,872 A | 11/1999 | Bourgeois |
| 5,998,386 A | 12/1999 | Feldman |
| 6,006,134 A | 12/1999 | Hill et al. |
| 6,007,559 A | 12/1999 | Arkans |
| 6,014,588 A | 1/2000 | Fitz |
| 6,018,682 A | 1/2000 | Rise |
| 6,042,538 A | 3/2000 | Puskas |
| 6,043,273 A | 3/2000 | Duhaylongsod |
| 6,060,454 A | 5/2000 | Duhaylongsod |
| 6,073,048 A | 6/2000 | Kieval et al. |
| 6,087,394 A | 7/2000 | Duhaylongsod |
| 6,091,988 A | 7/2000 | Warman et al. |
| 6,101,412 A | 8/2000 | Duhaylongsod |
| 6,103,722 A | 8/2000 | Schultz et al. |
| 6,127,410 A | 10/2000 | Duhaylongsod |
| 6,134,470 A | 10/2000 | Hartlaub |

(56) References Cited

U.S. PATENT DOCUMENTS

| | | | |
|---|---|---|---|
| 6,141,589 A | 10/2000 | Duhaylongsod |
| 6,141,590 A | 10/2000 | Renirie et al. |
| 6,167,305 A | 12/2000 | Cammilli et al. |
| 6,185,459 B1 | 2/2001 | Mehra et al. |
| 6,221,851 B1 | 4/2001 | Feldman |
| 6,234,985 B1 | 5/2001 | Lurie et al. |
| 6,253,108 B1 | 6/2001 | Rosborough et al. |
| 6,256,537 B1 | 7/2001 | Stoop et al. |
| 6,259,947 B1 | 7/2001 | Olson et al. |
| 6,266,564 B1 | 7/2001 | Hill et al. |
| 6,272,380 B1 | 8/2001 | Warman et al. |
| 6,299,564 B1 | 10/2001 | Gessler et al. |
| 6,303,293 B1 | 10/2001 | Patterson et al. |
| 6,304,777 B1 | 10/2001 | Ben-Haim et al. |
| 6,381,499 B1 | 4/2002 | Taylor et al. |
| 6,393,316 B1 | 5/2002 | Gillberg et al. |
| 6,414,018 B1 | 7/2002 | Duhaylongsod |
| 6,429,217 B1 | 8/2002 | Puskas |
| 6,438,421 B1 | 8/2002 | Stahmann et al. |
| 6,442,429 B1 | 8/2002 | Hill et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,532,388 B1 | 3/2003 | Hill et al. |
| 6,537,540 B1 | 3/2003 | Burstein et al. |
| 6,542,774 B2 | 4/2003 | Hill et al. |
| 6,554,781 B1 | 4/2003 | Carter et al. |
| 6,572,895 B2 | 6/2003 | Smith et al. |
| 6,587,719 B1 | 7/2003 | Barrett et al. |
| 6,589,954 B1 | 7/2003 | Mavunkel et al. |
| 6,609,025 B2 | 8/2003 | Barrett et al. |
| 6,611,713 B2 | 8/2003 | Schauerte |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,656,960 B2 | 12/2003 | Puskas |
| 6,690,973 B2 | 2/2004 | Hill et al. |
| 6,711,436 B1 | 3/2004 | Duhaylongsod |
| 6,718,208 B1 | 4/2004 | Hill et al. |
| 6,721,603 B2 | 4/2004 | Zabara et al. |
| 6,731,978 B2 | 5/2004 | Olson et al. |
| 6,735,471 B2 | 5/2004 | Hill et al. |
| 6,738,667 B2 | 5/2004 | Deno et al. |
| 6,778,854 B2 | 8/2004 | Puskas |
| RE38,654 E | 11/2004 | Hill et al. |
| RE38,705 E | 2/2005 | Hill et al. |
| 6,850,801 B2 | 2/2005 | Kieval et al. |
| 6,889,077 B2 | 5/2005 | Bornzin et al. |
| 6,904,318 B2 | 6/2005 | Hill et al. |
| 6,912,419 B2 | 6/2005 | Hill et al. |
| 7,138,607 B2 | 11/2006 | Wang et al. |
| 7,139,607 B1 | 11/2006 | Shelchuk |
| 7,200,438 B2 | 4/2007 | Euler |
| 7,225,019 B2 | 5/2007 | Jahns et al. |
| 7,231,254 B2 | 6/2007 | DiLorenzo |
| 7,245,967 B1 | 7/2007 | Shelchuk |
| 7,269,457 B2 | 9/2007 | Shafer et al. |
| 7,299,091 B2 | 11/2007 | Barrett et al. |
| 7,321,793 B2 | 1/2008 | Ben Ezra et al. |
| 7,493,161 B2 | 2/2009 | Libbus et al. |
| 7,499,748 B2 | 3/2009 | Moffitt et al. |
| 7,509,166 B2 | 3/2009 | Libbus |
| 7,542,800 B2 | 6/2009 | Libbus et al. |
| 7,548,780 B2 | 6/2009 | Libbus et al. |
| 7,555,341 B2 | 6/2009 | Moffitt et al. |
| 7,555,345 B2 | 6/2009 | Wahlstrand et al. |
| 7,587,238 B2 | 9/2009 | Moffit et al. |
| 7,643,875 B2 | 1/2010 | Heil, Jr. et al. |
| 7,711,421 B2 | 5/2010 | Shafer et al. |
| 7,840,278 B1 | 11/2010 | Puskas |
| 8,032,215 B2 | 10/2011 | Libbus et al. |
| 8,036,741 B2 | 10/2011 | Jahns et al. |
| 8,036,756 B2 | 10/2011 | Swoyer et al. |
| 2001/0049543 A1 | 12/2001 | Kroll |
| 2002/0035335 A1 | 3/2002 | Schauerte |
| 2002/0049478 A1* | 4/2002 | Ding et al. ............ 607/17 |
| 2002/0072782 A1 | 6/2002 | Osorio et al. |
| 2002/0107553 A1 | 8/2002 | Hill et al. |
| 2002/0198570 A1 | 12/2002 | Puskas |
| 2002/0198571 A1 | 12/2002 | Puskas |
| 2003/0045909 A1 | 3/2003 | Gross et al. |
| 2003/0060857 A1 | 3/2003 | Perrson et al. |
| 2003/0074039 A1 | 4/2003 | Puskas |
| 2003/0216775 A1 | 11/2003 | Hill et al. |
| 2003/0216790 A1 | 11/2003 | Hill et al. |
| 2004/0024422 A1 | 2/2004 | Hill et al. |
| 2004/0059383 A1 | 3/2004 | Puskas |
| 2004/0111118 A1 | 6/2004 | Hill et al. |
| 2004/0162584 A1 | 8/2004 | Hill et al. |
| 2004/0172075 A1 | 9/2004 | Shafer et al. |
| 2004/0186517 A1 | 9/2004 | Hill et al. |
| 2004/0186531 A1 | 9/2004 | Jahns et al. |
| 2004/0199209 A1 | 10/2004 | Hill et al. |
| 2005/0096707 A1 | 5/2005 | Hill et al. |
| 2005/0119704 A1 | 6/2005 | Peters et al. |
| 2005/0143412 A1 | 6/2005 | Puskas |
| 2006/0074450 A1 | 4/2006 | Boveja et al. |
| 2006/0095081 A1 | 5/2006 | Zhou et al. |
| 2006/0106429 A1 | 5/2006 | Libbus et al. |
| 2006/0173494 A1 | 8/2006 | Armstrong et al. |
| 2006/0206159 A1 | 9/2006 | Moffitt et al. |
| 2006/0224202 A1 | 10/2006 | Moffitt et al. |
| 2006/0293712 A1 | 12/2006 | Kieval et al. |
| 2007/0021792 A1 | 1/2007 | Kieval et al. |
| 2007/0021796 A1 | 1/2007 | Kieval et al. |
| 2007/0021799 A1 | 1/2007 | Kieval et al. |
| 2007/0083242 A1 | 4/2007 | Mazgalev et al. |
| 2007/0106337 A1 | 5/2007 | Errico et al. |
| 2008/0058872 A1* | 3/2008 | Brockway et al. ............ 607/2 |
| 2008/0091240 A1 | 4/2008 | Ben-David et al. |
| 2008/0234780 A1 | 9/2008 | Smith et al. |
| 2008/0269819 A1* | 10/2008 | Zhou ............................. 607/14 |
| 2008/0300640 A1 | 12/2008 | Mazgalev et al. |
| 2009/0234408 A1 | 9/2009 | Moffitt et al. |
| 2010/0036447 A1 | 2/2010 | Zhang et al. |
| 2010/0114208 A1 | 5/2010 | Donofrio et al. |
| 2011/0004262 A1 | 1/2011 | Bianchi et al. |
| 2011/0270332 A1 | 11/2011 | Buschman et al. |
| 2011/0270342 A1 | 11/2011 | Buschman et al. |
| 2011/0270343 A1 | 11/2011 | Buschman et al. |
| 2012/0029586 A1 | 2/2012 | Kumar et al. |
| 2012/0029587 A1 | 2/2012 | Zhou et al. |
| 2012/0029600 A1 | 2/2012 | Zhou et al. |
| 2012/0185007 A1 | 7/2012 | Ziegler et al. |
| 2012/0185008 A1 | 7/2012 | Zhou et al. |
| 2012/0185009 A1 | 7/2012 | Kornet et al. |
| 2012/0185010 A1 | 7/2012 | Zhou et al. |

FOREIGN PATENT DOCUMENTS

| | | |
|---|---|---|
| CA | 2310183 | 8/1998 |
| CA | 2 376 903 A1 | 1/2001 |
| DE | 2811325 | 9/1979 |
| EP | 0440111 A2 | 8/1991 |
| EP | 0547734 A2 | 6/1993 |
| EP | 0562408 A1 | 9/1993 |
| EP | 0589252 A2 | 3/1994 |
| EP | 1 051 168 | 2/1999 |
| EP | 0756507 B1 | 2/1999 |
| EP | 1 005 337 | 3/1999 |
| EP | 1181947 A2 | 2/2002 |
| EP | 1426078 A1 | 6/2004 |
| EP | 1 005 337 B1 | 5/2005 |
| EP | 1 051 168 B1 | 3/2006 |
| EP | 1870129 A1 | 12/2007 |
| JP | 2000507363 | 8/1998 |
| JP | 2001505980 | 6/2000 |
| MX | PA00002043 | 3/2004 |
| WO | WO 92/11064 A1 | 7/1992 |
| WO | WO 97/40885 A1 | 2/1997 |
| WO | WO 97/13550 A1 | 4/1997 |
| WO | WO 99/09973 A1 | 8/1998 |

(56) References Cited

FOREIGN PATENT DOCUMENTS

| | | |
|---|---|---|
| WO | WO 99/00057 A1 | 1/1999 |
| WO | WO 99/07354 A2 | 2/1999 |
| WO | WO 99/09971 A1 | 3/1999 |
| WO | WO 99/63926 A2 | 12/1999 |
| WO | WO 00/01306 A1 | 1/2000 |
| WO | WO 00/09206 A1 | 2/2000 |
| WO | WO 01/00273 A1 | 2/2001 |
| WO | WO 01/89526 A1 | 11/2001 |
| WO | WO 02/26320 A1 | 4/2002 |
| WO | WO 03/103484 A2 | 12/2003 |
| WO | WO 03/103484 A3 | 4/2004 |
| WO | WO 2007/142563 A1 | 12/2007 |
| WO | WO 2008/0144125 A1 | 11/2008 |

OTHER PUBLICATIONS

Agnew et al., "Considerations for Safety with Chronically Implanted Nerve Electrodes," *Epilepsia*, 1990; 31(Suppl. 2):S27-S32.

Ando et al., "Efferent Vagal Nerve Stimulation Protects Heart Against Ischemia-Induced Arrhythmias by Preserving Connexin43 Protein," *Circulation*, 2005; 112:164-170.

Annegers et al., "Epilepsy, Vagal Nerve Stimulation by the NCP System, All-Cause Mortality, and Sudden, Unexpected, Unexplained Death," *Epilepsia*, 2000; 41(5):549-553.

"Atrial Fibrillation: Current Understandings and Research Imperatives," the National Heart, Lung, and Blood Institute Working Group on Atrial Fibrillation, *JACC*, Dec. 1993; 22(7):1830-1834.

Barwell et al., "The NIM-2 Nerve Integrity Monitor in Thyroid and Parathyroid Surgery," *British Journal of Surgery*, 1997; 84:854.

Beekwilder et al., "Overview of the Clinical Applications of Vagus Nerve Stimulation," *Journal of Clinical Neurophysiology*, Apr. 2010; 27(2):130-138.

Bell et al., "Intropic Response of the Left Ventricle to Changes in Heart Rate in Anesthetized Rabbits," *Can.J. Physiol. Pharmacol.*, 1987; 65(2):179-184.

Bennetti, "Direct Coronary Surgery with Saphenous Vein Bypass Without Either Cardiopulmonary Bypass or Cardiac Arrest," *J. Cardiovasc. Surg.*, 1985; 26:217-222.

Bennetti et al., "Use of Thoracoscopy and a Minimal Thoracotomy, in Mammary-Coronary Bypass to Left Anterior Descending Artery, Without Extracorporeal Circulation," *J. Cardiovasc. Surg.*, Apr. 1995; 36(2):159-161.

Ben-Menachem et al., "Vagus Nerve Stimulation for Treatment of Partial Seizures: 1. A Controlled Study of Effect on Seizures," *Epilepsia*, 1994; 35(3):616-626.

Besedovsky et al., "Immunoregulatory Feedback Between Interleukin-1 and Glucocorticoid Hormones," *Science*, Aug. 8, 1986; 233(4764):652-654.

Bianchi et al., "Endocardial Transcatheter Stimulation of the AV Node Fat Pad: Stabilization of Rapid Ventricular Rate Response During Atrial Fibrillation in Left Ventricular Failure" *Journal of Cardiovascular Electrophysiology*, Jan. 2009; 20(1):103-105. Epub Jul. 3, 2008.

Bilgutay et al. "Vagal Tuning—A New Concept in the Treatment of Supraventricular Arrhythmias, Angina Pectoris, and Heart Failure," Jul. 1968, *Journal of Thoracic and Cardiovascular Surgery*, vol. 56, No. 1, pp. 71-82.

Binks et al., "High Strength Stimulation of the Vagus Nerve in Awake Humans: a Lack of Cardiorespiratory Effects," *Respiration Physiology*, 2001; 127:125-133.

Bluemel et al., "Parasympathetic Postganglionic Pathways to the Sinoartrial Node," *Am. J. Physiol.*, 1990; 259(5 Pt 2):H1504-H1510.

Borovikova et al., "Role of Vagus Nerve Signaling in CNI-1493-Mediated Suppression of Acute Inflammation," *Autonomic Neuroscience: Basic and Clinical*, 2000; 85:141-147.

Borovikova et al., "Vagus Nerve Stimulation Attenuates the Systemic Inflammatory Response to Endotoxin," *Nature*, 2000; 405(6785):458-462.

Braunwald et al., "Carotid Sinus Nerve Stimulation in the Treatment of Angina Pectoris and Supraventricular Tachycardia," *California Medicine: The Western Journal of Medicine*, 1970; 112(3):41-50.

Bristow, "The Adrenergic Nervous System in Heart Failure," *The New Eng. J. of Med.*, Sep. 27, 1984; 311(13):850-851.

Brodde et al., "Cardiac Muscarinic Receptors Decrease with Age: In Vitro and In Vivo Studies," *Journal of Clinical Investigations*, Jan. 1998; 101(2):471-478.

Bufkin et al., "Controlled Intermittent Asystole: Parmacologic Potentiation of Vagal-Induced Asystole," *Ann.Thorac. Surg.*, 1998; 66:1185-1190.

Buschman et al., "Control of Heart Rate with Vagus Nerve Stimulation," 7th Annual Conference of the International Functional Electrical Stimulation Society (IFESS), Ljubijana, Slovenia, Jun. 25-29, 2002. Abstract not available.

Buschman et al., "Heart Rate Control Via Vagus Nerve Stimulation," *Neuromodulation*, Jul. 2006; 9(3):214-220.

Carlson et al., "Selective Stimulation of Parasympathetic Nerve Fibers to the Human Sinoatrial Node," *Circulation*, Apr. 1992; 85(4):1311-1317.

Carlsson et al., "Therapy of Atrial Fibrillation: Rhythm Control Versus Rate Control," *PACE*, May 2000; 23:891-903.

Chiou, "Efferent Vagal Innervation of the Canine Atria and Sinus and Atrioventricular Nodes: The Third Fat Pad" *Circulation*, 1997; 95:2573-2584.

Clarke et al., Cognitive Motor Function After Electrical Stimulation of the Vagus Nerve, *PACE*, Oct. 1992; 15(10 PartII):1603-1607.

Clarke et al., "Acute Effects of High Frequency Vagal Nerve Stimulation on Balance and Cognitive Motor Performance in Epilepsy: Three Case Study Reports," *PACE*, Oct. 1992; 15(10 PartII):1608-1613.

Clarke et al., "Electrostimulation Effects of the Vagus Nerve on Balance in Epilepsy," *PACE*, Oct. 1992; 15(10 PartII):1614-1630.

Cooper et al., "Neural Effects on Sinus Rate and Atrioventricular Conduction Produced by Electrical Stimulation from a Transvenous Electrode Catheter in the Canine Right Pulmonary Artery," *Circulation Research*, Jan. 1980; 46(1):48-57.

Daubert et al., "Inappropriate Implantable Cardioverter-Defibrillator Shocks in MADIT II: Frequency, Mechanisms, Predictors, and Survival Impact," *J. Am. Coll. Cardiol.*, 2008; 51:1357-1365.

DiMarco et al., "Adenosine: Electrophysiologic Effects and Therapeutic Use for Terminating Paroxysmal Supraventricular Tachycardia," *Circulation*, Dec. 1983; 68(6):1254-1263.

Dipiro et al., Editor, "Pharmacotherapy: A Pathophysiologic Approach," 1989; 153-157.

Diwan et al., "Inflammatory Mediators and the Failing Heart: A Translational Approach," *Cur. Mol. Med.*, 2003; 3(2):161-182.

Donaldson et al., "Velocity-selective recording using multi-electrode nerve cuffs," 7th Annual Conference of the International Functional Electrical Stimulation Society (IFESS), Ljubijana, Slovenia, Jun. 25-29, 2002; 5 pgs.

Duhaylongsod et al., "Controlled Ventricular Asystole with Surgeon-Actuated Pacing for Off-Pump Coronary Artery Bypass Grafting: A Proposed Surgical Method," Presentation Summary, Presented at International Society for Minimally Invasive Cardiac Surgery Annual Meeting, Jun. 25, 1998, Minneapolis, MN, 1 page.

Eckberg, "The Human Respiratory Gate" *J. Physiol.*, 2003; 548. 2:339-352.

Espinosa et al., "Revision and Removal of Stimulating Electrodes Following Long-Term Therapy with the Vagus Nerve Stimulator," *Surgical Neurology*, 1999; 51: 659-664.

Fanning et al., "Reoperative Coronary Artery Bypass Grafting Without Cardiopulmonary Bypass," *Ann. Thorac. Surg.*, Feb. 1993; 55(2):486-489.

Finkel et al., "Negative Inotropic Effects of Cytokines on the Heart Mediated by Nitric Oxide," *Science*, Jul. 17, 1992; 257(5068):387-389.

Fleshner et al., "Thermogenic and Corticosterone Responses to Intravenous Cytokines (IL-1β and TNF-α) are Attenuated by Subdiaphragmatic Vagotomy," *J. of Neuroimmunology*, 1998; 86:134-141.

Freilich et al., "Adenosine and its Cardiovascular Effects," *American Heart Journal*, May 1992; 123(5):1324-1328.

(56) References Cited

OTHER PUBLICATIONS

Garcia-Perez et al., "Effect of Stimulating Non-myelinated Vagal Axons on Atrio-ventricular Conduction and Left Ventricular Function in Anaesthetized Rabbits," *Autonomic Neuroscience: Basic and Clinical*, 2001; 86:183-191.
Garnett et al., "Regional Cerebral Blood Flow in Man Manipulated by Direct Vagal Stimulation," *PACE*, Oct. 1992; 15(10 PartII):1579-1580.
Gaykema et al., "Subdiaphragmatic Vagotomy Suppresses Endotoxin-Induced Activation of Hypothalamic Corticotropin-Releasing Hormone Neurons and ACTH Secretion," *Endocrinology*, Oct. 1995; 136(10):4717-4720.
George et al., "Vagus Nerve Stimulation for Treatment of Partial Seizures: 3. Long-Term Follow-Up on First 67 Patients Exiting a Controlled Study," *Epilepsia*, 1994; 35(3):637-643.
Gorman et al., "How New Heart-Scanning Technology Could Save Your Life," *Time*, Sep. 5, 2005; 8 pages.
Guarini et al., "Efferent Vagal Fibre Stimulation Blunts Nuclear Factor-kB Activation and Protects Against Hypovolemic Hemorrhagic Shock," *Circulation*, Mar. 4, 2003; 107(8):1189-1194.
Gulick et al., "Interleukin 1 and Tumor Necrosis Factor Inhibit Cardiac Myocyte β-adrenergic Responsiveness," *Proc. Natl. Acad. Sci. USA*, Sep. 1989; 86(17):6753-6757.
Gupta, "Suppression of Paroxysmal Atrial Fibrillation by Pacing," *Indian Pacing and Electrophysiology Journal*, 2003; 3(2):45-46.
Hageman et al., "Direct and Reflex Cardiac Bradydysrhythmias From Small Vagal Nerve Stimulations," *Am. Heart J.*, Mar. 1975; 89(3):338-348 (Abstract only).
Hammond et al., "Vagus Nerve Stimulation in Humans: Neurophysiological Studies and Electrophysiological Monitoring," *Epilepsia*, 1990; 31(Suppl. 2):S51-S59.
Harvey et al., "Radiofrequency Catheter Ablation for Atrial Fibrillation," *Coronary Artery Disease*, 1995; 6:115-120.
Henning et al., "Vagal Nerve Stimulation Increases Right Ventricular Contraction and Relaxation and Heart Rate," *Cardiovascular Research*, 1996; 32:846-853.
Hirota et al., "Loss of gp130 Cardiac Muscle Cell Survival Pathway is a Critical Event in the Onset of Heart Failure during Biomechanical Stress," *Cell*, 1999; 97:189-198.
Holder et al., "Treatment of Refractory Partial Seizures: Preliminary Results of a Controlled Study," *PACE*, Oct. 1992; 15(10 PartII):1557-1571.
Israel et al., "Atrial Pacing in the Prevention of Paroxysmal Atrial Fibrillation: First Results of a New Combined Algorithm," *PACE*, Nov. 2000, Part II; 23:1888-1890.
Jalife et al., "Desensitization of the Cholinergic Receptor at the Sinoatrial Cell of the Kitten," *Am. J. Physiol.*, 1980; 238(4):H439-448.
Jones, "Vagal Control of the Rat Heart," *Exp. Physiol.*, Nov. 2001; 86(6):797-801.
Kale et al., "Atrial Septal Pacing in the Prevention of Paroxysmal Atrial Fibrillation Refractory to Antiarrhythmic Drugs," *International Journal of Cardiology*, 2002; 82:167-175.
Kamath et al., "Neurocardiac Responses to Vagoafferent Electrostimulation in Humans," *PACE*, Oct. 1992; 15(10 PartII):1581-1587.
Kandel et al., Editors, Principles of Neural Science, Fourth Edition, McGraw-Hill, New York, 2000. Title page, copyright page and table of contents, 29 pgs.
Khanna et al., "Coronary Artery Surgery with Induced Temporary Asystole and Intermittent Ventricular Pacing: An Experimental Study," *Cardiovascular Surgery*, Apr. 1996, 4(2):231-236.
Klassen et al., "Coronary Venous Pressure and Flow: Effects of Vagal Stimulation, Aortic Occulsion and Vasodialators," *Can. J. Physiol. Pharmacol.*, May 1984; 62(5):531,538.
Kornet et al., "Stimulation of the Intra-Cardiac Vagal Nerves Innervating the AV-Node to Control Ventricular Rate During AF: Specificity, Parameter Optimization and Chronic Use up to 3 Months," *J. Interv. Card. Electrophysiol.*, Jan. 2012; 33(1):7-18. Published online Oct. 4, 2011.

Krown et al., "Tumor Necrosis Factor Alpha-Induced Apoptosis in Cardiac Myocytes: Involvement of the Sphingolipid Signaling Cascade in Cardiac Cell Death," *J. Clin. Invest.*, 1996; 98(12):2854-2865.
Lagi et al., "Age-Related Changes of Cardiac Parasympathetic Modulation After Vasovagal Syncope," *American Journal of Cardiology*, Mar. 15, 1999; 83:977-980.
Laperche et al., "Potential Interests of Heart Rate Lowering Drugs" *Heart*, 1999; 81:336-341.
Levine et al., "Pacing for the Suppression of Paroxysmal Atrial Fibrillation in an 87-year-old Patient," *Indian Pacing and Electrophysiology Journal*, 2003; 3(2):88-90.
Levy et al., "Autonomic Control of Cardiac Pacemaker Activity and Atrioventricular Transmission," *Journal of Applied Physiology*, Oct. 1969; 27(4):465-470.
Levy et al., "Parasympathetic Control of the Heart," Chapter 4, Nervous Control of Cardiovascular Function, Oxford University Press, New York, 1984, pp. 68-94.
Li et al., "Myocardial Extracellular Matrix Remodeling in Transgenic Mice Overexpressing Tumor Necrosis Factor α can be modulated by Anti-Tumor Necrosis Factor α Therapy," *PNAS*, Nov. 7, 2000; 97(23):12746-12751.
Li et al, "Vagal Nerve Stimulation Markedly Improves Long-Term Survival after Chronic Heart Failure in Rats," *Circulation*, 2004; 109:120-124.
Lisman et al., "The Role of Tumor Necrosis Factor Alpha Blockade in the Treatment of Congestive Heart Failure," *CHF*, Sep./Oct. 2002; pp. 275-279.
Lockard et al., "Feasibility and Safety of Vagal Stimulation in Monkey Model," *Epilepsia*, 1990; 31(Supp. 2):S20-S26.
Loeb et al., "Sensitivity Differences of SA and AV Node to Vagal Stimulation: Attenuation of Vagal Effects at SA Node," *Am. J. Physiol.*, Nov. 1981; 241(5):H684-H690.
McGregor et al., "Proteomics of Heart Disease," *Human Molecular Genetics*, Oct. 15, 2003; 12(Review Issue 2):R135-R144.
Maloney et al., "A New Method for Intraoperative Recurrent Laryngeal Nerve Monitoring," *ENT Journal*, 1994; 73(1):30-33.
Mann, "Mechanisms and models in Heart Failure—A Combinatorial Approach," *Circulation*, Aug. 31, 1999; 100(9):999-1008.
Mann et al., "New Therapeutics for Chronic Heart Failure," *Annu. Rev. Med.*, 2002; 53:59-74.
Martin et al., "Fade of Cardiac Responses During Tonic Vagal Stimulation," *Am. J Physiol.*, 1982; 243(2):H219-H225.
Matheny et al., "Vagus Nerve Stimulation as a Method to Temporarily Slow or Arrest the Heart," Presented at the Second Utrecht MICABG Workshop, Oct. 4-5, 1996, Utrecht, Netherlands. Transcription of Presentation. *Annals of Thoracic Surgery*, Jun. 6, 1997; 63(6):S28-S29.
Matheny, "Techniques of Stabilization," Experiences in Minimally Invasive Surgery Conference, Jun. 19-21, 1997, Minneapolis, MN. Transcription of Presentation, 6 pages.
Mitchell, "The Role of Pacemaker and Defibrillator Therapy for the Treatment of Atrial Fibrillation," *Minerva Cardioangiologica*, Apr. 2004, 52(2):141-153.
Mohiuddin et al., "Safety of different Dosages of Intravenous Adenosine Used in Conjunction with Diagnostic Myocardial Imaging Techniques," *Pharmacotherapy*, Sep./Oct. 1993; 13(5):476-480.
Murgatroyd, "Pills and Pulses: Hybrid Therapy for Atrial Fibrillation," *Journal of Cardiovascular Electrophysiology*, Jan. 2002; 13(1) Suppl:S40-S46.
Nanthakumar et al., "Inappropriate Therapy from Atrial Fibrillation and Sinus Tachycardia in Automated Implantable Cardioverter Defibrillators," *American Heart Journal*, May 2000; 139(5):797-803.
Naritoku et al., "Chronic Vagus Nerve Stimulation Increases the Latency of the Thalamocortical Somatosensory Evoked Potential," *PACE*, Oct. 1992; 15(10 PartII):1572-1578.
Nerheim et al., "Heart Failure and Sudden Death in Patients with Tachycardia-Induced Cardiomyopathy and Recurrent Tachycardia," *Circulation*, 2004; 110:247-252.
Nobrega et al., "Resting and Reflex Heart Rate Responses During Cholinergic Stimulation with Pyridostigmine in Humans," *Braz. J. Med. Biol. Res.*, Nov. 1996; 29(11):1461-1465 (Abstract Only).

(56) References Cited

OTHER PUBLICATIONS

Noonan, "And the Beat Goes on," *Newsweek*, Jul. 11, 2005, pp. 56-57.
Nunain et al., "Limitations and Late Complications of Third-Generation Automatic Cardioverter-Defibrillators," *Circulation*, 1995; 91:2204-2213.
Ogawa et al., "Acute Effects of Different Atrial Pacing Sites in Patients with Atrial Fibrillation: Comparison of Single Site and Biatrial Pacing," *PACE*, Oct. 2001; 24:1470-1478.
Okazawa et al., "Effect of Vagal Stimulations and Parenteral Acetylcholine on Canine Trachealis Muscle Shortening," *J. Appl. Physiol.*, 1992; 75(6):2463-2468, (Abstract Only).
Ordelman et al., "Average Reference Recording from the Vagal Nerve Reveals an Evoked Indirect Response" Proceedings of the 4th International IEEE EMBS Conference on Neural Engineering Antalya, Turkey, Apr. 29-May 2, 2009.
Ordelman et al., "An Evoked Indirect Response in the Cervical Vagal Nerve" 4th Annual Symposium of the IEEE-IMBS Benelux Chapter, Nov. 9-10, 2009, Enschede, The Netherlands; p. 28.
Ordelman et al., "An Indirect Component in the Evoked Compound Action Potential of the Vagal Nerve" *J. Neural. Eng.*, 2010; 7:1-9.
Ousdigian et al., "Continuous ICD Diagnostics Triage Patients for Urgent Intervention: Low vs. High Risk of Inappropriate Shocks for AF," Heart Rhythm Society Congress 2008, 29th Annual Scientific Sessions, May 14-17, 2008, San Francisco, CA.
Pavlov et al., "Central Muscarinic Cholinergic Regulation of the Systemic Inflammatory Response during Endotoxemia," *PNAS*, Mar. 28, 2006; 103(13):5219-5223.
Penry et al., "Prevention of Intractable Partial Seizures by Intermittent Vagal Stimulation in Humans: Preliminary Results," *Epilepsia*, 1990; 31(Suppl.2):S40-S43.
Pfister et al., "Coronary Artery Bypass Without Cardiopulmonary Bypass," *Ann. Thorac. Surg.*, Dec. 1992; 54(6):1085-1092.
Poller et al., "Age-Dependent Changes in Cardiac Muscarinic Receptor Function in Healthy Volunteers," *Journal of American College of Cardiology*, Jan. 1997; 29(1):187-193.
Poole et al., "Prognostic Importance of Defibrillator Shocks in Patients with Heart Failure," *New England Journal of Medicine*, Sep. 4, 2008, 359:1009-1017.
Puglisi et al., "Persistent Atrial Fibrillation Worsens Heart Rate Variability, Activity and Heart Rate, as Shown by a Continuous Monitoring by Implantable Biventricular Pacemakers in Heart Failure Patients," *Journal of Cardiovascular Electrophysiology*, Jul. 2008; 19(7):693-701.
Pulkki, "Cytokines and Cardiomyocyte Death," *Annals of Medicine*, 1997; 29:339-343.
Purefellner et al., "Accuracy of Atrial Tachyarrhythmia Detection in Implantable Devices with Arrhythmia Therapies," *PACE*, Jul. 2004; 27:983-992.
Puskas, Declaration/Clarification of John D. Puskas, MD, dated Oct. 11, 2005, 7 pgs.
Ramsay et al., "Vagus Nerve Stimulation for Treatment of Partial Seizures: 2. Safety, Side Effects, and Tolerability," *Epilepsia*, 1994; 35(3):627-636.
Randall et al., "Functional Anatomy of the Cardiac Efferent Innervation," *Neurocardiology*, 1988; pp. 3-24.
Reid, "Surgical Technique for Implantation of the Neurocybernetic Prosthesis," *Epilepsia*, 1990; 31(Suppl. 2):S38-S39.
Ricci et al., "Efficacy of a Dual Chamber Defibrillator with Atrial Antitachycardia Functions in Treating Spontaneous Atrial Tachyarrhythmias in Patients with Life-Threatening Ventricular Tachyarrhythmias" *European Heart Journal*, 2002; 23:1471-1479.
Rieger et al., "Experimental determination of compound action potential direction and propagation velocity from multi-electrode nerve cliffs" *Medical Engineering & Physics*, 2004; 26: 531-534.
Rosenqvist et al., "Relative Importance of Activation Sequence Compared to Atrioventricular Synchrony in Left Ventricular Function," *The American Journal of Cardiology*, Jan. 15, 1991; 67:148-156.
Rossi et al., "Post-Operative Atrial Fibrillation Management by Selective Epicardial Vagal Fat Pad Stimulation" *J. Interv. Card. Electrophysiol.*, 2009; 24:37-45.
Rossi et al., "Vagal Tone Augmentation to the Atrioventricular Node in Humans: Efficacy and Safety of Burst Endocardial Stimulation" *Heart Rhythm*, May 2010; 7(5):683-689.
Rossi et al., "Endocardial Vagal Atrioventricular Node Stimulation in Humans: Reproducibility on 18-Month Follow-up," *Europace*, 2010; 12:1719-1724. Published online on Sep. 27, 2010.
Roy et al., "Rhythm Control Versus Rate Control for Atrial Fibrillation and Heart Failure," *The New England Journal of Medicine*, Jun. 19, 2008; 358(25):2667-2677.
Rutecki, "Anatomical, Physiological, and Theoretical Basis for the Antiepileptic Effect of Vagus Nerve Stimulation," *Epilepsia*, 1990; 31(Suppl. 2):S1-S6.
Saksena et al., "Prevention of Atrial Fibrillation by Pacing," Chapter 6 in *Recent Advances in Cardiac Pacing: Goals for the 21st Century*, Barold et al., Eds., 1998, Armonk, NY. Cover page, copyright page and pp. 101-114.
Sato et al., "Age-Related Changes of Cardiac Control Function in Man," *Journal of Gerontology*, 1981; 36(5):564-572.
Schwartz et al., "Long Term Vagal Stimulation in Patients with Advanced Heart Failure: First Experience in Man," *European Journal of Heart Failure*, 2008; 10:884-891.
Severtson et a., "Vagal Nerve Monitoring: A Comparison of Techniques in a Canine Model," *American Journal of Otology*, 1997; 18(3):398-400.
Sharma et al., "The Importance of Tumor Necrosis Factor and Lipoproteins in the Pathogenesis of Chronic Heart Failure," *Heart Failure Monitor*, 2001; 2(2):42-47.
Shishehbor et al., "Inflammation: Implications for Understanding the Heart-Brain Connection," *Cleveland Clinic Journal of Medicine*, Feb. 2007; 74(Suppl 1): S37-S41.
Subramanian, "Clinical Experience with Minimally Invasive Reoperative Coronary Bypass Surgery," *Eur. J. Cardio-Thorac. Surg.*, 1996, 10:1058-1062. (Abstract Only).
Tan et al., "Cardiac Myocyte Necrosis Induced by Angiotensin II," *Circulation Research*, 1991; 69(5):1185-1195.
Tarver et al., "Clinical Experience with a Helical Bipolar Stimulating Lead," *PACE*, Oct. 1992; 15(10 PartII):1545-1556.
Taylor, "Anticholinesterase Agents," Goodman and Gilman's Pharmacological Basis of Therapeutics, 6th Ed. MacMillian Publishing Co., Inc., New York, 1980; pp. 104-108.
Taylor, "Multiple-electrode Nerve Cuffs for Low-velocity and Velocity-selective Neural Recording," *Med. Biol. Eng. Comput.*, 2004; 42:634-643.
Terry et al., "An Implantable Neurocybernetic Prosthesis System," *Epilepsia*, 1990; 31(Suppl. 2):S33-S37.
Thompson et al., "Bradycardia Induced by Intravascular Versus Direct Stimulation of the Vagus Nerve," *Ann. Thorac. Surg.*, 1998; 65:637-642.
Tosato et al., "Closed-loop Control of the Heart Rate by Electrical Stimulation of the Vagus Nerve," *Med. Biol. Eng. Comput.*, 2006; 44:161-169.
Tougas et al., "Effects of Chronic Left Vagal Stimulation on Visceral Vagal Function in Man," *PACE*, Oct. 1992; 15(10 PartII):1588-1596.
Tougas et al., "Evidence of Impaired Afferent Vagal Function in Patients with Diabetes Gastroparesis," *PACE*, Oct. 1992; 15(10 PartII):1597-1602.
Tracey, "Physiology and Immunology of the Cholinergic Antiinflammatory Pathway," *The Journal of Clinical Investigation*, Feb. 2007; 117(2):289-296.
Upton, Editorial, *PACE*, Oct. 1992; 15(10 PartII):1543-1544.
Urthaler, "Experimental Studies on Pathogensis of Asystole After Verapamil in the Dog," *Am. J. Cardiol.*, Oct. 1979; 44(4):651-656 (Abstract Only).
Uthman et al., "Efficacy and Safety of Vagus Nerve Stimulation in Patients with Complex Partial Seizure," *Epilepsia*, 1990, 31(Suppl. 2):S44-S50.
Vardas et al., "AAIR Versus DDDR Pacing in Patients with Impaired Sinus Node Chronotropy: An Echocardiographic and Cardiopulmonary Study," *PACE*, Jul. 1997; 20:1762-1768.

(56) References Cited

OTHER PUBLICATIONS

Watkins et al., "Implications of Immune-to-Brain Communications for Sickness and Pain," *Proc. Natl. Acad Sci. USA*, Jul. 1999; 96:7710-7713.

Watkins et al., "Glia: A Novel Drug Discovery Target for Clinical Pain," Nature Reviews Drug Discovery, 2003; 2:973-985.

Westaby, "Coronary Surgery Without Cardiopulmonary Bypass," *British Heart Journal*, 1995; 73:203-205.

Wilder, "Vagus Nerve Stimulation for the Control of Epilepsy," Epilepsia, vol. 31, Supplement 2, 1990, pp. S1-S60; Conference Proceedings in conjunction with American Epilepsy Society Annual Meeting, Boston, MA, Dec. 2, 1989. Cover pages, Table of Contents, Foreword, and Summary and Conclusions; 6 pgs. (Each article listed in the Table of Contents is included separately in this Information Disclosure Statement).

Wilkoff et al., "Critical Analysis of Dual-Chamber Implantable Cardioverter-Defibrillator Arrhythmia Detection," *Circulation*, Jan. 23, 2001, 103(3):381-386.

Woodbury et al., "Effects of Vagal Stimulation on Experimentally Induced Seizures in Rats," *Epilepsia*, 1990; 31(Suppl. 2):S7-S19.

Yeh et al., "Geriatric Cachexia: The Role of Cytokines," *Am. J Clin. Nutr.*, 1999; 70:183-197.

Yokoyama et al., "Cellular Basis for the Negative Inotropic Effects of Tumor Necrosis Factor-α in the Adult Mammalian Heart," *The Journal of Clinical Investigation*, Nov. 1993; 92:2303-2312.

Yokoyama et al., "Tumor Necrosis Factor-α Provokes a Hypertrophic Growth Response in Adult Cardiac Myocytes," *Circulation*, 1997; 95:1247-1252.

Zhang et al., "Optimal Ventricular Rate Slowing During Atrial Fibrillation by Feedback AV Nodal-Selective Vagal Stimulation" *Am. J. Physiol. Heart Circ. Physiol.*, 2002; 282:H1102-H1110.

Zhang et al., "Achieving Regular Slow Rhythm During Atrial Fibrillation Without Atrioventricular Nodal Ablation: Selective Vagal Stimulation Plus Ventricular Pacing" *Heart Rhythm*, 2004; 1(4):469-475.

Zhang et al., "Chronic Atrioventricular Nodal Vagal Stimulation: First Evidence for Long-Term Ventricular Rate Control in Canine Atrial Fibrillation Model," *Circulation*, 2005; 112:2904-2911.

Zhuang et al., "Ventricular Rate Control by Selective Vagal Stimulation is Superior to Rhythm Regularization by Atrioventricular Nodal Ablation and Pacing During Atrial Fibrillation," *Circulation*, 2002; 106:1853-1858.

International Search Report, PCT/US/2008/059723, Aug. 27, 2008, 6 pgs.

Written Opinion, PCT/US/2008/059723, Aug. 27, 2008, 7 pgs.

International Preliminary Report on Patentability, PCT/US/2008/059723, Oct. 27, 2009, 8 pgs.

International Search Report and Written Opinion, PCT/EP2010/003956, dated Nov. 4, 2010, 11 pgs.

Reply to Written Opinion, PCT/EP2010/003956 (WO 2011/000558) dated May 2, 2011, 4 pgs.

International Preliminary Report on Patentability, PCT/EP2010/003956, dated Jul. 20, 2011, 10 pgs.

Office Action for U.S. Appl. No. 11/740,565, mailed Dec. 30, 2009, 8 pages.

Responsive Amendment to Office Action for U.S. Appl. No. 11/740,565, filed Apr. 29, 2010, 11 pages.

Final Office Action for U.S. Appl. No. 11/740,565, mailed Jan. 21, 2011, 9 pages.

Responsive Amendment to Office Action for U.S. Appl. No. 11/740,565, filed Mar. 21, 2011, 8 pages.

US 6,184,239, 02/2001, Puskas (withdrawn)

\* cited by examiner

VAGAL STIMULATION

CROSS-REFERENCE TO RELATED APPLICATIONS

This application claims the benefit of U.S. Provisional Application No. 61/434,279, filed on Jan. 19, 2011. The disclosure of the above application is incorporated herein by reference in its entirety.

BACKGROUND

The disclosure herein relates to methods for treating heart conditions using vagal stimulation, and further to devices for performing such treatment. For example, methods and devices to initiate, prevent, and/or adjust the delivery of vagal stimulation based on monitored physiological parameters.

The use of nerve stimulation, e.g., stimulation of the vagus nerve, for treating and controlling a variety of medical, psychiatric, and neurological disorders has seen significant growth over the last several decades, e.g., including the treatment of heart conditions. The vagus nerve is composed of somatic and visceral afferent fibers (which, e.g., convey impulses toward the brain) and efferent fibers (which, e.g., convey impulses to an effector to regulate activity such as muscle contraction or glandular secretion).

The rate of the heart may be restrained in part by parasympathetic stimulation from the right and left vagus nerves. Low vagal nerve activity may be related to various arrhythmias, including tachycardia, ventricular accelerated rhythm, and rapid atrial fibrillation.

SUMMARY

The disclosure herein relates generally to methods for treating heart conditions using vagal stimulation, and further to systems and devices for performing such treatment. Such methods may include monitoring physiological parameters of a patient, detecting cardiac conditions, and delivering vagal stimulation (e.g., electrical stimulation to the vagus nerve or neurons having parasympathetic function) to the patient to treat the detected cardiac conditions.

One exemplary device for delivering cardiac therapy disclosed herein includes monitoring apparatus, a sensing module, a therapy delivery module, and a control module. The monitoring apparatus is configured to monitor physiological parameters of a patient and includes at least one electrode to monitor the electrical activity of the patient's heart and at least one sensor to monitor the pressure of a ventricle of the patient's heart. The sensing module is coupled to the monitoring apparatus and is configured to receive the monitored physiological parameters. The therapy delivery module is configured to deliver electrical stimulation to the patient's vagus nerve. The control module is coupled to the sensing module and to the therapy delivery module. Further, the control module is configured to control the delivery of electrical stimulation to the patient's vagus nerve based on the monitored electrical activity and monitored ventricular pressure of the patient's heart.

In one or more embodiments of the exemplary devices disclosed herein, the control module is further configured to initiate the delivery of electrical stimulation to the patient's vagus nerve if the monitored P-R interval of the electrical activity of the patient's heart is less than a selected P-R value and the monitored ventricular pressure of the patient's heart is less than a selected pressure value to regulate the preload of the ventricles of the patient's heart. Further, the control module may be further configured to control the delivery of electrical stimulation to the patient's vagus nerve to be synchronized to blanking periods associated with either of the P-waves or the R-waves within the electrical activity of the patient's heart.

Further, in one or more embodiments of the exemplary devices disclosed herein, the control module is further configured to: determine whether the patient's cardiac condition is worsening after the delivery of electrical stimulation to the patient's vagus nerve; and terminate the delivery of electrical stimulation to the patient's vagus nerve if the patient's cardiac condition is worsening. For example, determining whether the patient's cardiac condition is worsening may include determining whether the monitored physiological parameters of the patient indicate at least one of atrial fibrillation, ventricular arrhythmia, mechanical functional deterioration, and syncope, and terminating the delivery of electrical stimulation to the patient's vagus nerve if the patient's cardiac condition is worsening may include terminating the delivery of electrical stimulation to the patient's vagus nerve if the monitored physiological parameters of the patient indicate at least one of atrial fibrillation, ventricular arrhythmia, mechanical functional deterioration, and syncope.

Still further, in one or more embodiments of the exemplary devices disclosed herein, the therapy delivery module is further configured to deliver electrical pacing therapy to the patient's heart and the control module is further configured to initiate the delivery of electrical pacing therapy to the patient's heart if the electrical activity of the patient's heart is indicative of heart failure. For example, the electrical activity of the patient's heart is indicative of heart failure if the monitored P-R interval of the electrical activity of the patient's heart is greater than a selected maximum P-R interval value. Further, the control module may be further configured to terminate the delivery of electrical pacing therapy to the patient's heart if the monitored P-R interval of the electrical activity of the patient's heart is less than a selected minimum P-R interval value.

One exemplary method for delivering cardiac therapy disclosed herein includes monitoring the electrical activity of a patient's heart, monitoring the ventricular pressure of the patient's heart, and delivering electrical stimulation to the patient's vagus nerve based on the electrical activity and ventricular pressure of the patient's heart. Delivering electrical stimulation to the patient's vagus nerve based on the electrical activity and ventricular pressure of the patient's heart may include initiating the delivery of electrical stimulation to the patient's vagus nerve if an average of the monitored P-R interval of the electrical activity of the patient's heart is less than a selected P-R value and the monitored ventricular pressure of the patient's heart is less than a selected pressure value to regulate the preload of the ventricles of the patient's heart.

In one or more embodiments of the exemplary methods disclosed herein, the delivery of electrical stimulation to the patient's vagus nerve is synchronized to blanking periods associated with either of the P-waves or the R-waves within the electrical activity of the patient's heart. Further, the exemplary methods further include determining whether the patient's cardiac condition is worsening after delivering electrical stimulation to the patient's vagus nerve and terminating the delivery of electrical stimulation to the patient's vagus nerve if the patient's cardiac condition is worsening. For example, determining whether the patient's cardiac condition is worsening may include determining whether the monitored physiological parameters of the patient indicate at least one of atrial fibrillation, ventricular arrhythmia, mechanical functional deterioration, and syncope and terminating the delivery of electrical stimulation to the patient's vagus nerve if the patient's cardiac condition is worsening may include terminating the delivery of electrical stimulation to the patient's vagus nerve if the monitored physiological parameters of the patient indicate at least one of atrial fibrillation, ventricular arrhythmia, mechanical functional deterioration, and syncope.

Further, in one or more embodiments of the exemplary methods disclosed herein, the exemplary methods further include delivering electrical pacing therapy to the patient's heart if the electrical activity of the patient's heart is indicative of heart failure. For example, the electrical activity of the patient's heart is indicative of heart failure if the monitored P-R interval of the electrical activity of the patient's heart is greater than a selected maximum P-R interval value. Further, the exemplary methods may further include terminating the delivery of electrical pacing therapy to the patient's heart if the monitored P-R interval of the electrical activity of the patient's heart is less than a selected minimum P-R interval value.

One exemplary device for delivering cardiac therapy disclosed herein includes monitoring apparatus, a sensing module, a therapy delivery module, and a control module. The monitoring apparatus is configured to monitor physiological parameters of a patient and includes at least one electrode to monitor the electrical activity of the patient's heart. The sensing module is coupled to the monitoring apparatus and configured to receive the monitored physiological parameters. The therapy delivery module is configured to deliver electrical stimulation to the patient's vagus nerve and to deliver electrical pacing therapy to the patient's heart. The control module is coupled to the sensing module and to the therapy delivery module. Further, the control module is configured to control the delivery of electrical stimulation to the patient's vagus nerve and to control the delivery of electrical pacing therapy to the patient's heart. The control module is further configured to switch between electrical stimulation to the patient's vagus nerve and electrical pacing therapy to the patient's heart based on the monitored electrical activity of the patient's heart.

In one or more embodiments of the exemplary devices disclosed herein, the monitoring apparatus further includes at least one sensor to monitor the pressure of a ventricle of the patient's heart, and the control module is further configured to initiate the delivery of electrical stimulation to the patient's vagus nerve if the monitored P-R interval of the electrical activity of the patient's is less than a selected P-R value and the monitored ventricular pressure of the patient's heart is less than a selected pressure value.

Further, in one or more embodiments of the exemplary devices disclosed herein, the control module is further configured to determine whether the patient's cardiac condition is worsening after the delivery of electrical stimulation or electrical pacing therapy and terminate the delivery of electrical stimulation or electrical pacing therapy if the patient's cardiac condition is worsening.

Still further, in one or more embodiments of the exemplary devices disclosed herein, the control module is further configured to initiate the delivery of electrical pacing therapy to the patient's heart if the electrical activity of the patient's heart is indicative of heart failure. For example, the electrical activity of the patient's heart is indicative of heart failure if the monitored P-R interval of the electrical activity of the patient's heart is greater than a selected maximum P-R interval value. Further, the control module may be further configured to terminate the delivery of electrical pacing therapy to the patient's heart if the monitored P-R interval of the electrical activity of the patient's heart is less than a selected minimum P-R interval value. Still further, the control module may be further configured to adjust the electrical pacing therapy to the patient's heart if the monitored P-R interval of the electrical activity of the patient's heart is greater than a selected minimum P-R interval value.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
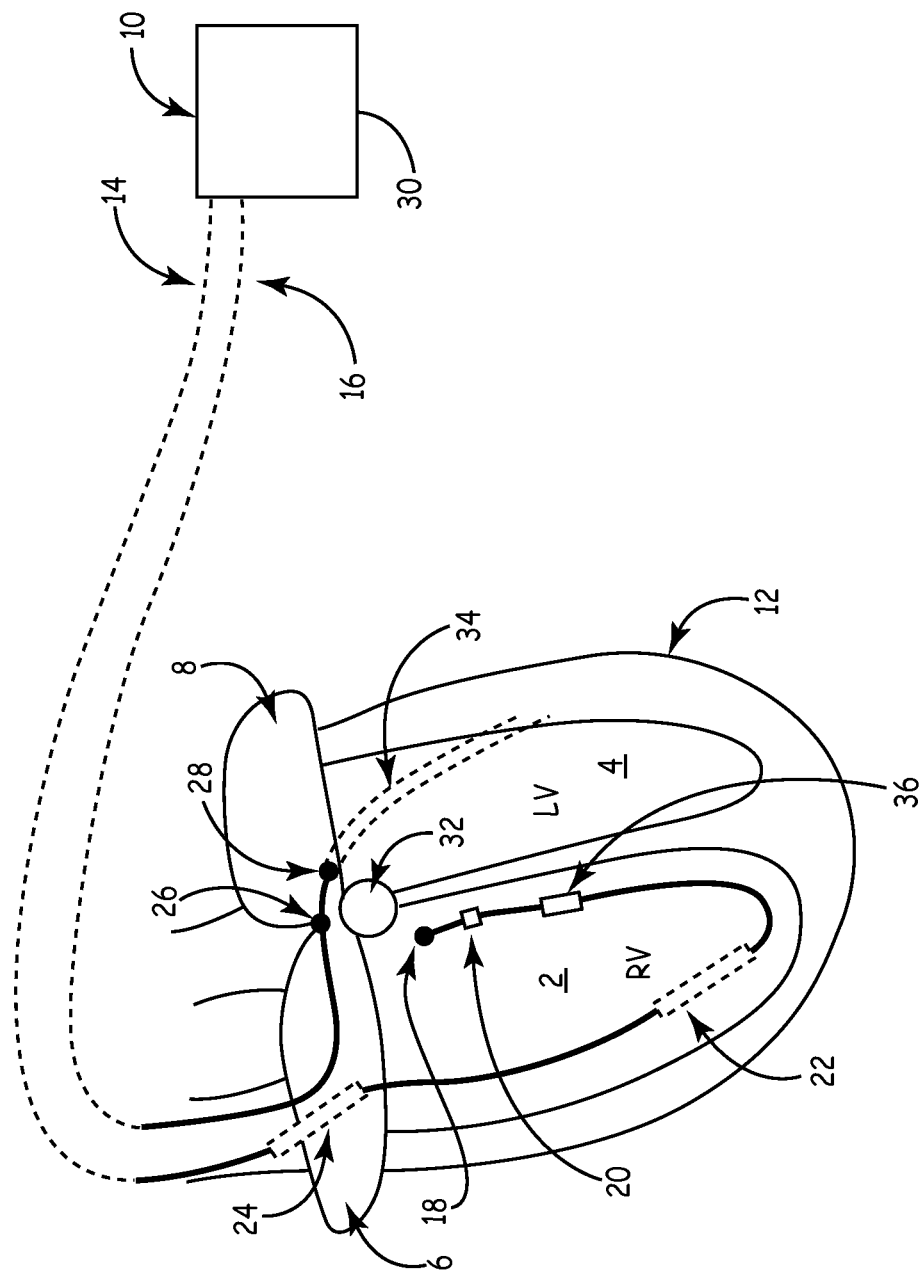
FIG. 1 is a schematic diagram of an implantable medical device (IMD) operably coupled to a patient's heart.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, devices, and systems shall be described with reference to FIGS. 1-15. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Abnormal autonomic nervous activities, such as an increased sympathetic tone and reduced parasympathetic tone, may contribute to the progression of heart failure and triggering of sudden cardiac death. Stimulation of the vagus nerve (e.g., the parasympathetic fibers of the vagus nerve) may reduce the progression of heart failure, may prevent recurring ventricular tachyarrhythmias, may decrease infarct size, may relieve myocardial ischemia, may assist in discriminating atrial tachyarrhythmia from ventricular arrhythmias, and may control ventricular rate during supraventricular tachyarrhythmias, etc.

More specifically, the parasympathetic tone of the vagus nerve may be increased by stimulating intracardiac parasympathetic neurons in the location such as fat pads near the superior vena cava (SVC) and inferior vena cava (IVC), tissue near the AV node, the base of the right ventricle, and vagal nerves near the heart, which, in turn may improve cardiac function, produce reversal remodeling, reduce myocardial ischemia, reduce myocardial infarct size, and protect the heart from life threatening arrhythmias. Further, the mechanisms for cardiac protection by intracardiac parasympathetic stimulation may involve inhibition of sympathetic activation, vagal anti-inflammatory effects, reduction of cardiac workload, improvement of tissue perfusion, anti-arrhythmic effects, induced hyperinnervation of the heart, maintenance of normal ventricular rate during supraventricular tachyarrhythmias, etc.

The methods described herein may be implemented by one or more various devices (e.g., implantable medical devices) and systems. Such devices and systems may include one or more leads, electronic circuits, power sources, sensors, electrodes, fluid delivery devices, etc. One example of a medical device that may be used in carrying out the methods described herein is depicted in FIG. 1 as a schematic diagram of an implantable medical device (IMD).

The IMD 10 may be configured to monitor one or more physiological parameters of a patient (e.g., electrical activity of a patient's heart, chemical activity of a patient's heart, hemodynamic activity of a patient's heart, and electrical activity of a patient's vagus nerve). The monitored physiological parameters, in turn, may be used by the IMD to detect various cardiac conditions, e.g., ventricular tachycardia (VT), ventricular fibrillation (VF), supraventricular ventricular tachycardia (SVT), atrial fibrillation (AF), atrial tachycardia (AT), myocardial ischemia/infarction, etc., and to treat such cardiac conditions with therapy. Such therapy may include delivering vagal stimulation (e.g., electrical stimulation to a patient's vagus nerve), electrical stimulation for pacing the patient's heart 12 (e.g., bradycardia pacing, cardiac resynchronization therapy, anti-tachycardia pacing (ATP), and/or other pacing therapies), etc. Further, in at least one embodiment, the IMD 10 may be capable of delivering high-energy shock pulses for cardioversion/defibrillation therapy delivered in response to, e.g., tachycardia detections.

As used herein, "stimulation of the vagus nerve," also referred to herein simply as "vagal stimulation," refers to stimulation of neural tissue innervating the myocardium, directly or indirectly, e.g., stimulation of one or more of the vagus nerves or its branches (e.g., including the afferent and/or efferent fibers), the sinoatrial (SA) nodal fatty pad, the atrioventricular (AV) nodal fatty pad and along the great vein, the cervical vagus nerve (e.g., the right or left side), the fat pad located between the medial superior vena cava and aortic root (SVC-Ao fat pad), the fat pad superior to the right pulmonary artery, the fat pad at the IVC-left atrial junction (IVC-LA fat pad), the fat pad proximate the right pulmonary vein-atrial junction (RPV fat pad), the septal region of the right atrium, the spinal cord (e.g., vertebral levels T1-T12, C1-C8, etc. such as described in U.S. Pat. App. Pub. No. 2002/0107552 A1 to Hill et al., which is incorporated herein by reference in its entirety), and additional intracardiac locations near the SA node, AV node, coronary sinus, and base of the right ventricle.

The IMD 10, as shown, is configured to monitor physiological parameters of the patient and to deliver therapy using two leads. Although the IMD 10 depicted in FIG. 1 only uses two leads, a single lead or more than two leads may be used with the methods, devices, and systems described herein. For example, the IMD 10 may use one lead that includes a single electrode positionable near the atrioventricular node in the base of the right ventricle. The single electrode may be used for both atrial/ventricular pacing/sensing and vagal recording/stimulation.

As shown, the IMD 10 is coupled to two transvenous leads: a right ventricular (RV) lead 14 and a coronary sinus (CS) lead 16. RV lead 14 includes a distal tip electrode 18 deployed in the basal region of the right ventricle 2 in operative relation to the AV node 32. Ring electrode 20 is spaced proximally from tip electrode 18 for use in bipolar sensing and pacing in the right ventricle 2. According to one embodiment, tip electrode 18 may be used in conjunction with IMD housing 30 (for unipolar sense/stimulation) or ring electrode 20 (for bipolar sense/stimulation) for sensing ventricular signals, for detecting a ventricular rhythm, for delivering cardiac pacing pulses in the right ventricle, for monitoring the ST segment, for recording/monitoring the electrical activity of the vagus nerve, and for delivering vagal stimulation pulses in the right ventricle (e.g., for discriminating SVT and VT). RV lead 14 may further include coil electrodes 22 and 24 for use in delivering high-energy shock pulses for cardioversion and defibrillation therapies. Other embodiments may include additional electrodes adapted for sensing and stimulating the right atrium 6, either on a separate right atrial lead or included along RV lead 14, recording the electrical activity of various nerves (e.g., the vagus nerve), etc. Further, such electrodes may be positioned relative to the SA node and or AV node for vagal stimulation or for recording/monitoring of the electrical activity of the vagus nerve (e.g., portions of the vagus nerve located in the heart 12).

RV lead 14 may further includes sensor 36 used for sensing signals other than cardiac electrical signals, such as mechanical signals, e.g., accelerometer sensing, hemodynamic activity, flow (idem), myocardial acceleration, heart sound, tissue perfusion, lung fluid status, etc., or blood chemistry signals, e.g., temperature, oxygen saturation, pH, etc. In one embodiment, sensor 36 is embodied as a pressure sensor (e.g., for monitoring various blood pressures and pressure drops) to, e.g., be used in verifying effective vagal stimulation. Further, for example, sensor 36 may be an oxygen sensor, as disclosed in U.S. Pat. No. 4,750,495 issued to Moore et al. on Jul. 31, 1989, a pressure transducer as disclosed in U.S. Pat. No. 4,485,813 issued to Anderson et al. on Dec. 4, 1984, a physical activity sensor as disclosed in U.S. Pat. No. 4,428,378, issued to Anderson et al on Jan. 31, 1984, or a ventricular impedance plethysmograph as disclosed in U.S. Pat. No. 4,535,774 issued to Olson on Aug. 20, 1985, all of which are incorporated herein by reference in their entireties.

Coronary sinus lead 16 may be deployed in a cardiac vein 34 via the coronary sinus for positioning electrodes 26 and 28 in operative relation to the left chambers of heart 12. In particular, in one embodiment, electrodes 26 and 28 are positioned near the AV node 32 to, e.g., allow electrical stimulation of the vagus nerve for discrimination of SVT and VT, for blocking conduction of the AV node 32, etc. Further, electrode 26 may be positioned proximate the coronary sinus. Electrodes 26 and 28 may also be used for sensing cardiac signals and for delivering cardiac pacing pulses in the left ventricle 4. It is recognized that coronary sinus lead 16 may carry additional electrodes such as a coil electrode for use in delivering high energy shock pulses, additional ring electrodes, and/or a tip electrode for cardiac sensing and pacing in the left atrium 8.

Furthermore, the embodiments described herein are not limited for use with transvenous leads as shown in FIG. 1. For example, other embodiments may include the use of epicardial electrodes positioned in operative relation to the fatty pad near the SA node and/or the fatty pad near the AV node. Further, subcutaneous electrodes may be incorporated on the housing 30 of IMD 10 and/or positioned on subcutaneous leads extending from IMD 10 for use in sensing cardiac signals and delivering electrical stimulation pulses, e.g., for delivering cardiac pacing and shock therapies. Numerous alternative electrode configurations may be appropriate for vagal stimulation, including endocardial or epicardial electrodes deployed near or adjacent the SA nodal and/or AV nodal fatty pads or electrodes positioned along the vagus nerve branches.

Figure 2:
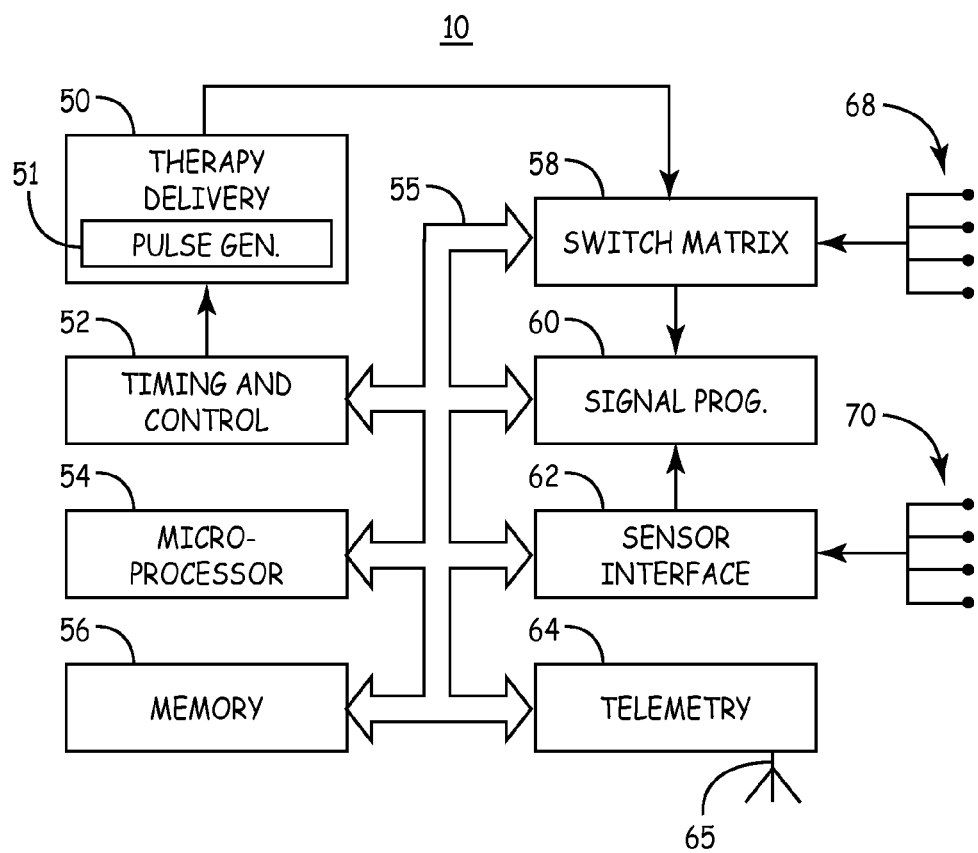
FIG. 2 is a block diagram of the IMD shown in FIG. 1.

FIG. 2 is a functional block diagram of IMD 10 shown in FIG. 1. IMD 10 generally includes timing and control circuitry 52 and an operating system that may employ microprocessor 54 or a digital state machine for timing sensing and therapy delivery functions and controlling other device functions in accordance with a programmed operating mode. Microprocessor 54 and associated memory 56 are coupled to the various components of IMD 10 via a data/address bus 55. IMD 10 includes therapy delivery module 50 for delivering a therapy, such as an electrical stimulation or drug therapy, under the control of timing and control circuitry 52. Therapy delivery module 50 includes pulse-generating circuitry 51 for generating electrical stimulation pulses (e.g., bursts of electrical stimulation pulses) under the control of timing and control circuitry 52. As will be described herein, pulse-generating circuitry 51 generates stimulation pulses for stimulating the vagus nerve.

For delivering electrical stimulation pulses, pulse-generating circuitry 51 may be coupled to two or more electrodes 68 via a switch matrix 58. Switch matrix 58 is used for selecting which electrodes and corresponding polarities are used for delivering electrical stimulation pulses. Electrodes 68 may include lead-based electrodes, leadless electrodes incorporated on IMD 10, and/or the IMD housing configured for use as a can or case electrode. Therapy delivery module 50 may further include high voltage circuitry for generating high voltage cardioversion/defibrillation shocks. Aspects of the present disclosure may be embodied in an implantable cardioverter defibrillator including high voltage circuitry as generally disclosed in U.S. Pat. No. 6,731,978 to Olson et al., incorporated herein by reference in its entirety.

Electrodes 68 may also be used for sensing electrical signals within the body, such as cardiac signals and/or nerve signals. Cardiac electrical signals are sensed using any of electrodes 68 for detecting the heart rhythm and determining when and what therapy is needed, and in controlling the timing of stimulation pulses. In other words, the IMD 10 includes monitoring apparatus, which includes electrodes 68 amongst other things. As will be described herein, cardiac electrical signals may be sensed following delivery of vagal stimulation for adjusting the vagal stimulation, for verifying the effectiveness of the vagal stimulation, and/or for detecting, and/or discriminating between cardiac conditions (e.g., SVT, VT/VF, etc.). Nerve signals are sensed using any of the electrodes 68 for detecting the electrical activity (e.g., parasympathetic activity, etc.) of various nerves.

Electrodes used for sensing and electrodes used for stimulation may be selected via switch matrix 58. When used for sensing, electrodes 68 are coupled to signal processing circuitry 60 via switch matrix 58. Processing circuitry 60 includes sense amplifiers and may include other signal conditioning circuitry and an analog to digital converter. In other words, the IMD 10 may include a sensing module, e.g., includes switch matrix 58, signal processing circuitry 60, etc. Electrically sensed signals may then be used by microprocessor 54 for detecting physiological events, such as detecting and discriminating cardiac arrhythmias.

The monitoring apparatus of the IMD 10 may further include sensors 70 such as pressure sensors, accelerometers, flow sensors, blood chemistry sensors, activity sensors, and/or other physiological sensors known for use with IMDs. Sensors 70 are coupled to IMD 10 via a sensor interface 62 which provides sensor signals to signal processing circuitry 60. Sensor signals are used by microprocessor 54 for detecting physiological events or conditions. For example, IMD 10 may monitor heart wall motion, blood pressure, blood chemistry, respiration, and/or patient activity. Monitored signals may be used for sensing the need for delivering, adjusting, terminating, and/or initiating therapy under control of the operating system. In other words, the IMD 10 may include a control module, which may include the microprocessor 54 and memory 56 and may be configured using an operating system.

The operating system includes associated memory 56 for storing a variety of programmed-in operating mode and parameter values that are used by microprocessor 54. The memory 56 may also be used for storing data compiled from sensed signals and/or relating to device operating history (e.g., for use in delivering, adjusting, controlling, initiating, and/or terminating therapy) and/or for communicating such data outside of the patient (e.g., using telemetry communication out of recorded history on receipt of a retrieval or interrogation instruction).

IMD 10 further includes telemetry circuitry 64 and antenna 65. Programming commands or data are transmitted during uplink or downlink telemetry between IMD telemetry circuitry 64 and external telemetry circuitry included in a programmer or home monitoring unit.

Figure 3:
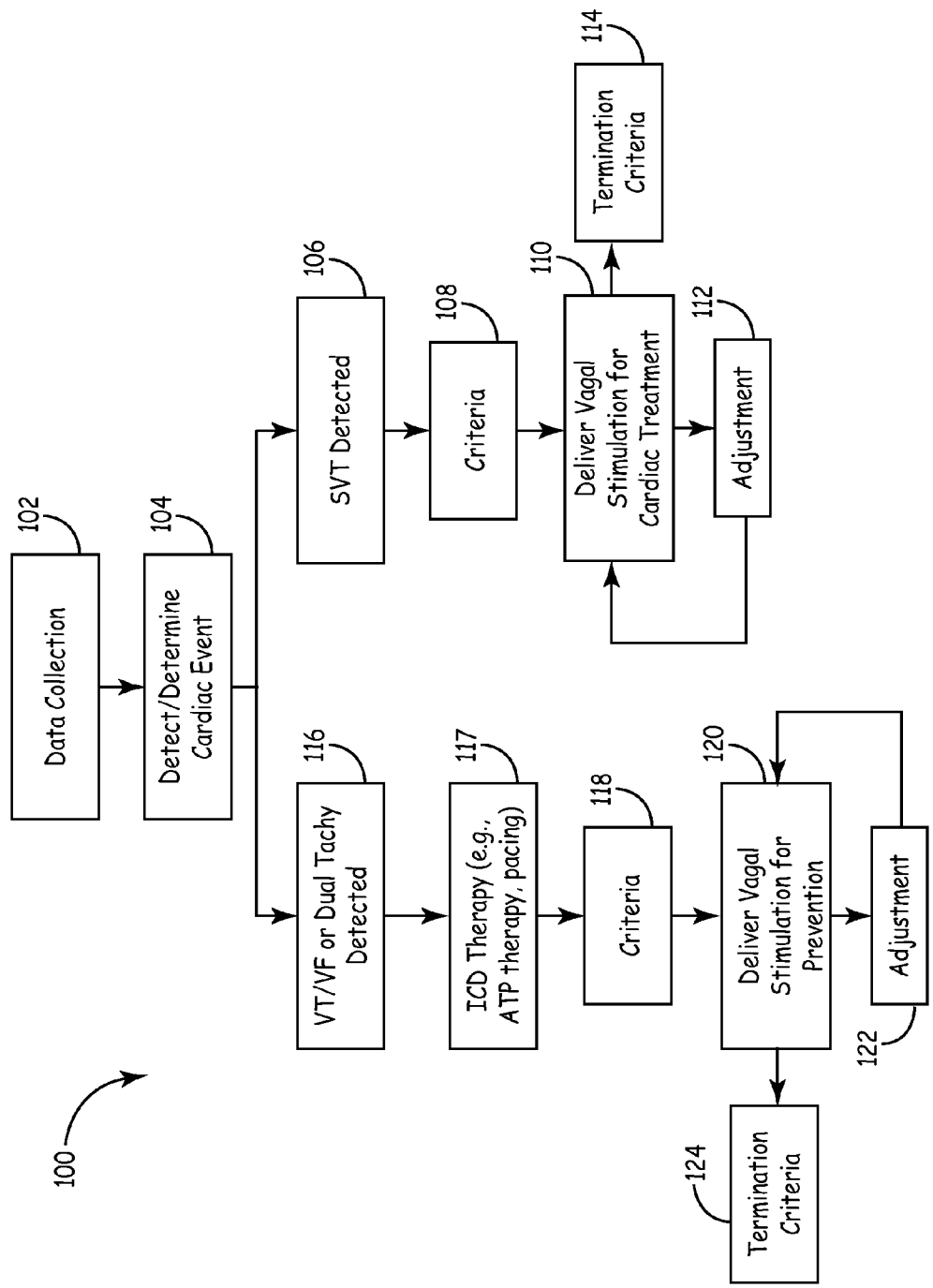
FIG. 3 is a flow chart depicting an exemplary general method of treating cardiac conditions, e.g., using vagal stimulation.

A generalized method 100 of treating cardiac conditions, e.g., using vagal stimulation, is diagrammatically depicted in FIG. 3. Method 100 is intended to illustrate the general functional operation of the devices and/or systems, and should not be construed as reflective of a specific form of software or hardware necessary to practice all of the methods described herein. It is believed that the particular form of software will be determined primarily by the particular system architecture employed in the device (e.g., IMD 10) and by the particular detection and therapy delivery methodologies employed by the device and/or system. Providing software and/or hardware to accomplish the described methods in the context of any modern IMD, given the disclosure herein, is within the abilities of one of skill in the art.

Further, methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The hardware used to accomplish the described methods, may include any one or more of a microprocessor, a digital signal processor (DSP), a controller, an application specific integrated circuit (ASIC), a field programmable gate array (FPGA), or equivalent discrete or integrated logic circuitry. In one or more exemplary embodiments, the processor may include multiple components, such as any combination of one or more microprocessors, one or more controllers, one or more DSPs, one or more ASICs, or one or more FPGAs, as well as other discrete or integrated logic circuitry. The functions and processes described herein may be embodied as software, firmware, hardware, or any combination thereof.

The method 100 of FIG. 3 includes data collection 102. Data collection 102 may include monitoring physiological parameters of a patient (e.g., at least one physiological parameter) such as, for example, the electrical activity of the patient's heart, the chemical activity of the patient's heart, the hemodynamic pressure of the patient's heart, the electrical activity of the patient's nerves, physical movement (e.g., using an accelerometer) of portions of the patient's heart, etc.

The electrical activity of a patient's heart may include one or more signals that may be monitored (e.g., using electrodes) from locations in or around the patient's heart. Using such monitored electrical activity of a patient's heart, certain metrics may be determined and collected (e.g., for analysis). For instance, the following metrics may be determined and collected using the electrical activity of the patient's heart: heart rate (HR), heart rate variability (HRV), heart rate turbulence (HRT), deceleration/acceleration capacity, deceleration sequence incidence, T-wave alternans (TWA), electrocardiogram, P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The chemical activity of a patient's heart may include one or more chemical properties that may be monitored (e.g., using various sensors) from locations in or around the patient's heart. Using such monitored chemical activity of a patient's heart, certain metrics may be determined and collected (e.g., for analysis). For instance, the following metrics may be determined and collected using the chemical activity of the patient's heart: oxygen saturation, brain natriuretic peptide (BNP) (proteins/peptides) content, pH, lung fluid status, blood electrolytes (K+, Ca++, Na+, etc.), etc.

The hemodynamic activity of a patient's heart may include one or more hemodynamic pressures that may be monitored (e.g., using various sensors) from locations in or around the patient's heart and/or in or around (e.g., outside of) the patient's body. Using such monitored hemodynamic pressures of a patient's heart, certain metrics may be determined and collected (e.g., for analysis). For instance, the following hemodynamic metrics may be determined and collected using the hemodynamic pressures of the patient's heart (e.g., using Medtronic OptiVol Fluid Status Monitoring): mean arterial pressure, diastolic blood pressure, systolic blood pressure, flow rates, pressure drops, pulmonary artery pressure, pulmonary capillary wedge pressure, right ventricular systolic pressure, right ventricular diastolic pressure, changes in oxygen saturation of the tissue or blood, changes in the amplitude or timing of heart sounds, changes in intrathoracic impedance (e.g. Medtronic OptiVol Fluid Status Monitoring), changes in intracardiac impedance, heart sounds, lung sounds, tissue perfusion, intracardiac pressure, pulmonary vein pressure, cardiac imaging, shear stress, partial pressure of oxygen, etc.

The nerve activity of a patient's heart may include one or more signals monitored (e.g., using electrodes) from locations in or around the patient's nerves. More specifically, the electrical signals propagating along the one or more nerve fibers of the patient's vagus nerve may be monitored. Such signals may include parasympathetic and sympathetic signals propagating along efferent and afferent nerve fibers.

The data collected 102 may be analyzed to detect and/or determine a cardiac event or condition 104. For example, the monitored physiological parameters may be indicative of cardiac arrhythmia, e.g., tachycardia (e.g., sinus tachycardia, VT/VF, SVT, AF, AV nodal reentrant tachycardia (AVNRT), AV reentrant tachycardia, junctional tachycardia, dual tachycardia, etc.), or heart failure decomposition. For example, methods of detecting and/or determining particular cardiac events or conditions have been disclosed, e.g., in U.S. Pat. App. Pub. No. 2008/0269819 A1 to Zhou, which is incorporated herein by reference in its entirety.

Although an arrow is shown in FIG. 3 extending from data collection 102 to cardiac event detection/determination 104, the data collection 102 and the cardiac event detection/determination 104 processes may be executed concurrently as opposed to sequentially or periodically.

If the analysis leads to a SVT being detected 106 (e.g., if the physiological parameters indicate that a patient is undergoing a SVT), the method 100 then evaluates criteria 108 before and/or during (e.g., periodically) the delivery of vagal stimulation to, e.g., treat the SVT. Methods that include analyzing physiological parameters for criteria and preventing the delivery of vagal stimulation if the criteria are not met are described in further detail herein, e.g., with reference to FIGS. 6-7, 9, and 12.

If the criteria are met, the method may deliver vagal stimulation 110. The stimulation may be delivered to the vagus nerve in many different ways. For example, the vagal stimulation may be delivered in bursts of pulses of electrical stimulation at various parameters. Such parameters may include time (e.g., the vagal stimulation may be delivered for a selected time period for each cardiac cycle), voltage (e.g., within a range of about 1 volt and about 8 volts), frequency of the pulses within a burst of pulses (e.g., within a range of about 1 hertz to about 150 hertz), frequency of the bursts (e.g., within a range of about 1 hertz to about 100 hertz if delivered continuously for cardiac stimulation—otherwise, each burst may be synchronized to the cardiac cycle or to P- or R-waves), pulse width of each pulse (e.g., within a range of about 0.05 milliseconds (ms) to about 1.5 ms), and number of pulses per burst (e.g., within a range of about 3 pulses to about 20 pulses), etc.

Figure 4A:
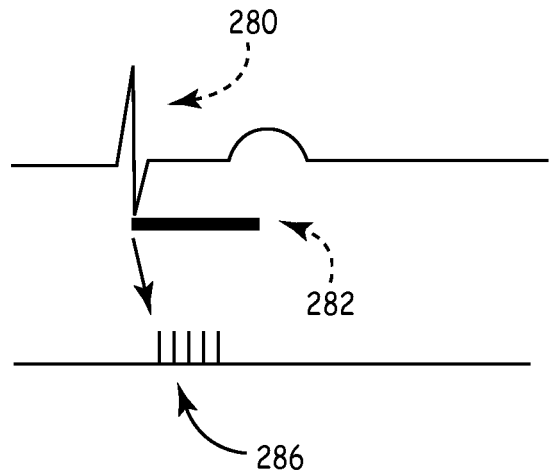
FIGS. 4A-4B are timing diagrams illustrating exemplary methods of synchronizing bursts of electrical stimulation to portions of the electrical activity of a patient's heart.
Figure 4B:
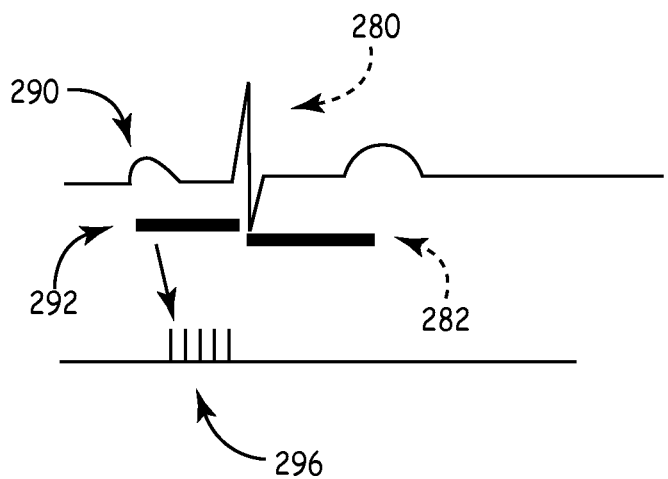

Further, the delivery of vagal stimulation 110 may be synchronized to blanking periods associated with either the P-waves or R-waves within the electrical activity of the patient's heart as shown in FIGS. 4A-4B. Also, in at least one embodiment, the delivery of vagal stimulation 110 may be synchronized to the patient's respiratory cycle or portions thereof. Still further, as described herein with reference to FIG. 1, the vagal stimulation may be delivered 100 to neural tissue innervating the myocardium, directly or indirectly, e.g., including the vagus nerve or its branches, the SA nodal fatty pad, the AV nodal fatty pad and along the great vein, the cervical vagus nerve (e.g., right or left side), the fat pad located between the medial superior vena cava and aortic root (SVC-Ao fat pad), and additional intracardiac locations near the SA node, AV node, coronary sinus, and base of the right ventricle.

The method 100 may further include adjusting the vagal stimulation 112 to, e.g., increase the effectiveness of the vagal stimulation, and may further include evaluating termination criteria 114 to, e.g., determine whether delivery of vagal stimulation to the patient should continue. Processes 110, 112, and 114 may run concurrently or periodically. For example, the method 100 may concurrently deliver vagal stimulation 110, periodically adjust the vagal stimulation 112, and continuously evaluate termination criteria 114. Methods that include adjusting the vagal stimulation 112 are described in further detail herein, e.g., with reference to FIGS. 5, 8, 11, and 13, and methods that include evaluating termination criteria 114 are described in further detail herein, e.g., with reference to FIGS. 6-10 and 12.

If analysis in method 100 results in a VT/VF or dual tachycardia detection 116 (e.g., if the physiological parameters indicate that a patient is undergoing VT/VF or dual tachycardia), the method 100 proceeds to deliver implantable cardioverter defibrillator (ICD) therapy 117 to, e.g., treat the VT/VF, or dual tachycardia. ICD therapy 117 may include high-energy shock pulses for cardioversion/defibrillation therapy, ATP and/or other pacing therapies. After the VT/VF or dual tachycardia has been treated (e.g., after it appears that the ICD therapy has successfully treated the VT/VF or dual tachycardia), the method 100 may proceed towards delivering vagal stimulation for prevention or protection 120 to, e.g., prevent recurring arrhythmias. A method, for example, that includes delivering vagal stimulation 112 for prevention is described in further detail herein, e.g., with reference to FIG. 10.

As shown, the method 100 further includes evaluating criteria 118 before and/or during (e.g., periodically) the delivery of vagal stimulation for prevention 120, and adjusting the vagal stimulation 122 and evaluating termination criteria 124 after or during the delivery of vagal stimulation for prevention 120. Processes 118, 122, and 124 may be, for example, substantially similar to processes 108, 112, and 114.

Electrical stimulation may be the most effective if delivered to the vagus nerve during periods corresponding to various cardiac events. FIGS. 4A-4B are timing diagrams illustrating the delivery of electrical stimulation (e.g., electrical stimulation pulses) to the patient's vagus nerve corresponding to various cardiac events. In particular, as shown in FIG. 4A, electrical stimulation pulses 286 (e.g., a burst of pulses) may be delivered to the patient's vagus nerve during the ventricular blanking interval 282 (also known as a ventricular blanking period or blanking period associated with R-waves) associated with or occurring after a ventricular event 280 (e.g., a sensed R-wave or a pacing pulse). Blanking interval 282 corresponds to a ventricular refractory period following a ventricular sensed or paced event 280. By delivering the electrical stimulation pulses 286 during the ventricular blanking interval 282, the same electrodes used for sensing ventricular activity and/or delivering ventricular pacing pulses may be used for delivering the electrical vagal stimulation. In this way, the electrical vagal stimulation may not occur during the ventricular vulnerable period; thereby avoiding arrhythmogenic effects associated with stimulating during the vulnerable period. The ventricular vulnerable period may be the time period within the cardiac cycle during which an electrical stimulation may cause arrhythmias, e.g., ventricular tachyarrhythmias (VT/VF). In other words, the heart may be the most susceptible to induction of VT/VF through stimulus during such vulnerable periods. Often, the ventricular vulnerable period occurs during the T-wave (e.g., the middle to the end of the T-wave). Prior to the vulnerable period is a refractory period during which stimulation may not cause arrhythmias (e.g., which may also correspond to the blanking periods). For example, when electrodes are positioned in the basal region of the right ventricle for delivering electrical stimulation pulses 286, the same electrodes may be used for sensing ventricular signals and/or delivering ventricular pacing pulses.

Further, as shown in FIG. 4B, electrical stimulation pulses 296 are delivered during the atrial blanking interval 292 (also known as an atrial blanking period or blanking period associated with P-waves) associated with or occurring after an atrial event 290 (e.g., a sensed P-wave or a pacing pulse). Blanking interval 292 corresponds to an atrial refractory period following an atrial sensed or paced event 290. By delivering the electrical stimulation pulses 296 during the atrial blanking interval 292, the same electrodes used for sensing atrial activity and/or delivering atrial pacing pulses may be used for delivering the electrical vagal stimulation. In this way, the electrical stimulation may not occur during the atrial vulnerable period (e.g., any atrial vulnerable period may be similar to the ventricular vulnerable period except that it relates to AF instead of VT/VF) thereby avoiding arrhythmogenic effects associated with stimulating during the vulnerable period. For example, when electrodes are positioned in the right atrium for delivering electrical stimulation pulses 296, the same electrodes may be used for sensing atrial signals and/or delivering atrial pacing pulses.

In one or more methods described herein, the vagal electrical stimulation may be synchronized to blanking periods associated with either or both of the P-waves and the R-waves within the electrical activity of the patient's heart. Further, for various reasons, the delivery of vagal stimulation may be adjusted to change the synchronization of the delivery of the vagal stimulation from one type of blanking period to another. For example, the delivery of vagal stimulation may be synchronized to the atrial P-waves and then changed to the ventricular R-waves or vice versa. In at least one embodiment, the vagal stimulation may be synchronized to the P-wave in sinus rhythm (e.g., delivery of electrical stimulation during the atrial blanking period) and switched/changed to be synchronized to the R-wave (e.g., delivery of electrical stimulation during the ventricular blanking period) when the patient's heart is in atrial fibrillation.

Vagal stimulation may be delivered after a fixed delay (e.g., a programmable delay) upon detection of a QRS complex, P-wave, or any other physiological parameter. As a result, when vagal stimulation is synchronized to a cardiac event, the vagal stimulation may be delivered during or after the cardiac event (e.g., after a fixed delay). Further, the processes described herein may further include checking that capture of cardiac tissue (e.g., as opposed to nerve tissue) has not occurred (e.g., by checking for the presence of an evoked response) or adjusting the stimulation parameters to avoid capture of cardiac tissue. Still further, the delay may be adaptive to optimize the efficacy of the vagal stimulation (e.g., a pulse train of vagal stimulation). For example, the delay may be adjusted to find the delay that has the greatest impact on cardiac behavior.

Figure 5:
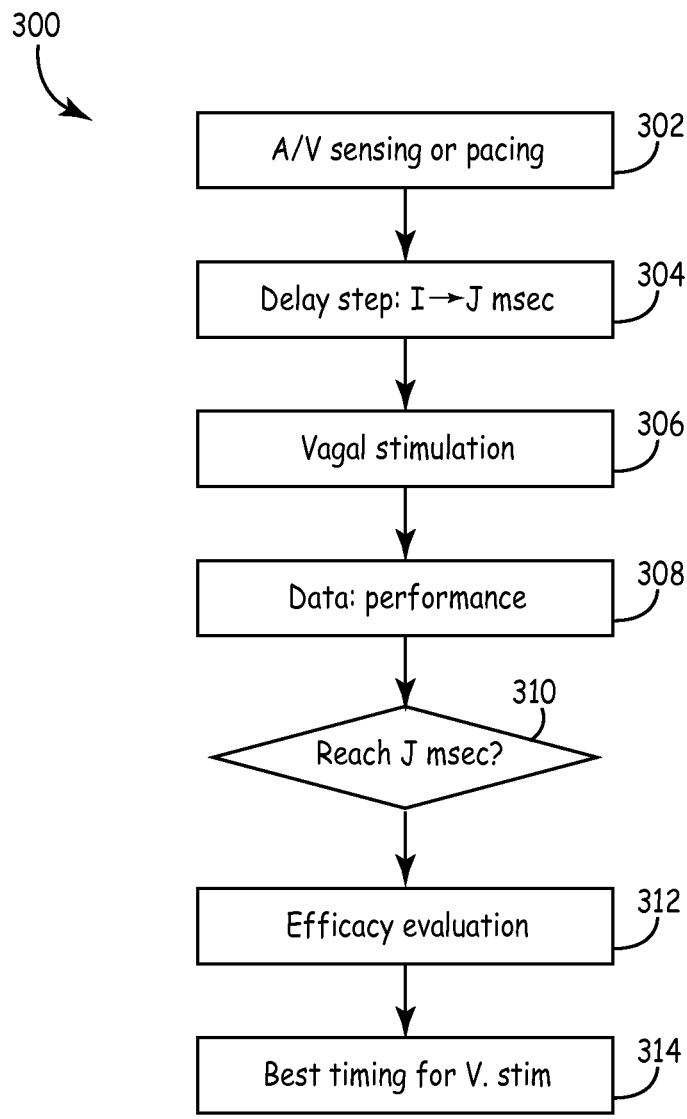
FIG. 5 is flow chart of an exemplary method of adjusting vagal stimulation for treating cardiac conditions.

FIG. 5 is a flow chart of an exemplary method 300 of adjusting vagal stimulation for treating cardiac conditions, for example, such as when a SVT has been detected or after ICD therapy has treated a VT/VF and vagal stimulation is to be provided for prevention of further arrhythmias. For example, the method 300 may include AN sensing or pacing of a patient's heart 302, which may be the general operation of the IMD implanted in the patient. For example, the IMD may be configured to monitor physiological parameters (e.g., the electrical activity of the patient's heart) and deliver ICD therapy if the physiological parameters indicate certain cardiac conditions such as, e.g., VT/VF.

Departing from the general AV sensing/pacing operation, the method 300 may include a delay step 304, which may be a period where the IMD departs from such operation. The period of the delay step 304 may be a selected time period or a selected number of heart beats of a patient. For example, the delay step 304 may be for about 50 ms to about 150 ms after either a P-wave or R-wave. Further, the delay step may be an optimal timing previously identified for effective stimulation at a low energy cost. During this delay step 304, the method 300 may deliver vagal stimulation 306 (e.g., subject to criteria). Delivery of vagal stimulation 306 may be substantially similar to the delivery of vagal stimulation 110 described herein with reference to FIG. 3.

During and/or after the delivery of vagal stimulation 306, the method 300 may record the performance data 308 of the patient (e.g., the physiological parameters of the patient including the electrical activity of the patient's heart) to be utilized in an evaluation of the efficacy of the vagal stimulation. For example, recording the performance data 308 may include recording the intervals between R-waves, intervals between P-waves and QRS complexes, R-wave morphology, ST segment, T wave morphology, hemodynamic changes, etc. Further, certain parameters of the vagal stimulation may be adjusted within certain ranges (e.g., the voltage, amplitude, number of pulses per burst, burst frequency, pulse frequency, pulse width, etc.) such that performance data may be recorded 308 for the vagal stimulation delivered at the various selected parameters (e.g., resulting in data for a plurality of different selected sets of parameters).

After the time period of the delay step has elapsed 310, the recorded performance data may be evaluated 312 to determine if the vagal stimulation was effective and/or what parameters of the vagal stimulation were the most effective. For example, the intervals between R-waves, the intervals between P-waves and QRS complexes, the R-wave morphology, ventricular pressure, etc. corresponding to the vagal stimulation (e.g., occurring during the delivery of vagal stimulation or directly after the delivery of vagal stimulation) may be compared to selected values. The selected values may be historical values recorded from the patient before the delivery of the vagal stimulation, standard baseline values of healthy cardiac activity, etc. In at least one embodiment, such comparisons may also simply look for an effect, e.g., a change in HR, from pre-stimulation to post-stimulation.

As a result of the evaluation 312, the method 300 may determine if vagal stimulation was effective and/or what parameters of vagal stimulation were the most effective in treating the patient 314 (e.g., the best timing). If a particular set of parameters of vagal stimulation are determined to be the most effective for treating the patient, such parameters may be stored, e.g., within an IMD, such that the most effective vagal stimulation may be delivered to the patient at a later time. Further, as a result of this method 300, an IMD may save energy, e.g., by not delivering ineffective vagal stimulation, by not constantly adjusting vagal stimulation for effectiveness, by finding effective vagal stimulation to take the place of some higher energy therapy, etc.

Figure 6:
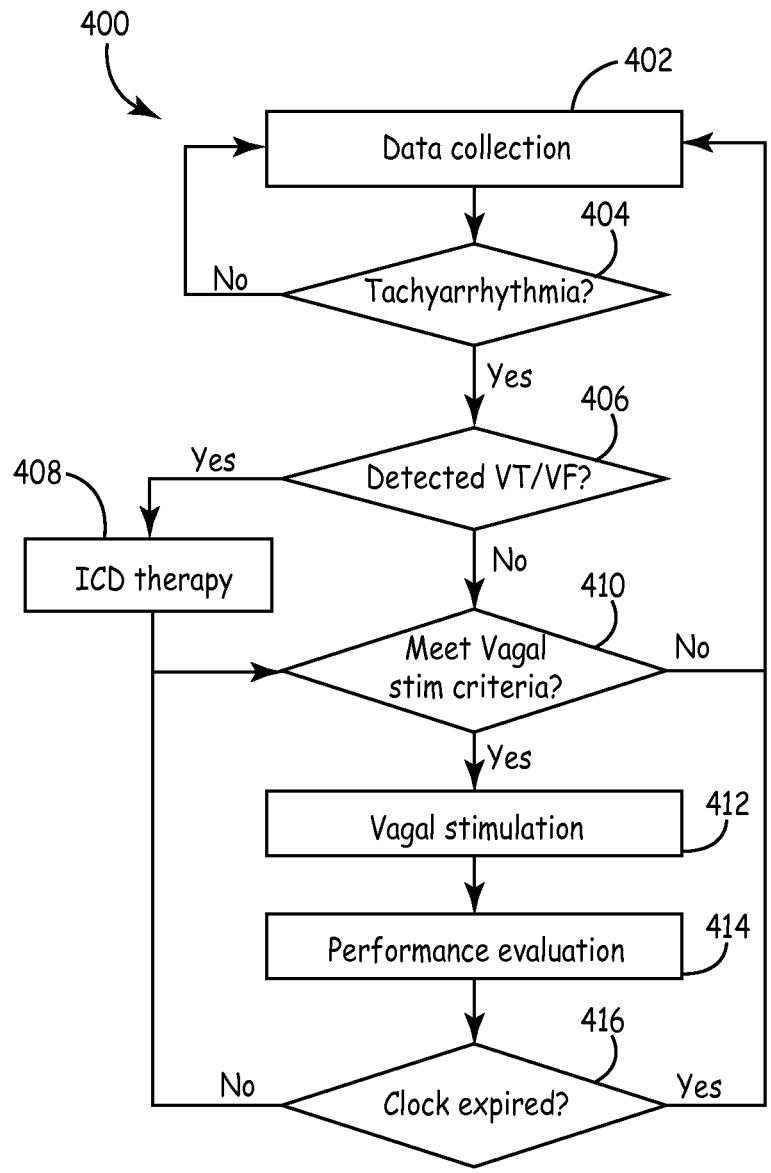
FIG. 6 is a flow chart of an exemplary method of delivering vagal stimulation and evaluating termination criteria.

FIG. 6 is a flow chart of another exemplary method 400 of treating heart conditions using vagal stimulation. The method 400 includes a data collection process 402, which may be substantially similar to data collection process 102 described herein with reference to FIG. 3. Periodically and/or concurrently with the data collection 402, the method 400 includes tachyarrhythmia detection 404 (e.g., a tachyarrhythmia may be detected from the physiological parameters of the patient monitored during the data collection 402). For example, a tachyarrhythmia may be detected if a patient's heart rate is higher than a selected value (e.g., about 150 beats/min to about 180 beats/min). If a tachyarrhythmia is detected, the method 400 will determine if the tachyarrhythmia is a VT/VF 406. In at least one embodiment, determining that the tachyarrhythmia is a VT/VF may include determining that ventricular rate exceeds approximately 150 beats per minute and such ventricular rate lasts for more than 10 heart beats. In at least another embodiment, determining that the tachyarrhythmia is a VT/VF may include determining whether the QRS morphology is indicative of normal sinus rhythm and/or determining whether the timing of atrial and ventricular activations is indicative of a sinus tachycardia or a supraventricular tachycardia (e.g., if the QRS morphology is not indicative of normal sinus rhythm and/or whether the timing of atrial and ventricular activations is not indicative of sinus tachycardia or supraventricular tachycardia, then the tachyarrhythmia may be VT/VF). In at least another embodiment, determining that the tachyarrhythmia is a VT/VF may include determining that a fast ventricular rate is sustained, that the R-wave morphology does not match a sinus or a SVT template, that the onset of the fast ventricular rate was not gradual or accompanied by a sudden P-R interval change in the case of a 1:1 rhythm, that the atrial and ventricular rates are dissociated in the case of fast atrial and ventricular rates, that the R-wave morphology is consistent with arrhythmia instead of noise, that the R-waves are not double counting, and/or that T-wave over-sensing is not occurring. Further criteria for determining VT/VF may be described in U.S. Pat. No. 5,545,186 issued on Aug. 13, 1996 to Olson et al., U.S. Pat. No. 5,991,656 issued on Nov. 23, 1999 to Olson et al., U.S. Pat. No. 6,259,947 issued on Jul. 10, 2001 to Olson et al., and U.S. Pat. No. 6,393,316 issued on May 21, 2002 to Gillberg et al., all of which are hereby incorporated by reference.

If the method 400 detects VT/VF, the method 400 proceeds to deliver ICD therapy 408 to the patient. ICD therapy 408 may be substantially similar to the ICD therapy 117 described herein with reference to FIG. 3.

Either after the VT/VF has been treated or if the tachyarrhythmia was not determined to be a VT/VF, the method 400 may proceed to determining if the patient meets various vagal stimulation criteria 410 (also referred to as criteria in one or more methods described herein) before delivering vagal stimulation 410. Foremost, the criteria process 410 may include a determination that a vagal stimulation-treatable cardiac condition is detected (e.g., such as a SVT). Methods of detecting and/or determining a SVT are described in U.S. Pat. App. Pub. No. 2008/0269819 A1 to Zhou, which is incorporated herein by reference in its entirety.

In at least one embodiment, the method 400 may include monitoring physiological parameters of a patient (e.g., the electrical activity of the patient's heart) and analyzing the monitored physiological parameters with respect to the criteria 410 such as vagal stimulation criteria (e.g., before delivering electrical stimulation 412 to the patient's vagus nerve). Analyzing the monitored physiological parameters may include determining whether the electrical activity of the patient's heart is indicative of a ventricular arrhythmia (e.g., a VT/VF), determining whether the lead configured to deliver electrical stimulation to the patient's vagus nerve is dislodged, and/or determining whether there is unrestrained sympathoexcitation (e.g., which may be indicated by an acceleration of heart rate (e.g., shortened V-V intervals, A-V intervals, V-T intervals, etc.)). Dislodgement of the lead configured to deliver electrical stimulation the patient's vagus nerve may lead to delivering electrical stimulation (e.g., bursts of electrical stimulation) in the ventricle, which may lead to an undesired VT. If the electrical activity of the patient's heart indicates a ventricular arrhythmia or if the lead configured to deliver electrical stimulation to the patient's vagus nerve is dislodged, process 410 will prevent the delivery of electrical stimulation to the patient's vagus nerve 412 (e.g., the method 400 will return to data collection 402).

One method of determining whether the lead configured to deliver electrical stimulation to the patient's vagus nerve is dislodged includes analyzing the electrical activity monitored by the lead or analyzing the effectiveness of the stimulation delivered by the lead. For example, if the electrical signal morphology changes from atrial-dominated morphology to ventricular morphology, then the lead may be dislodged. Further, for example, if the A-V interval monitored by the lead increases, the lead may be dislodged (e.g., the lead may have slipped into the ventricle). Still further, for example, if a threshold for effectiveness of vagal stimulation increases (e.g., vagal stimulation must be increased to be effective) or if the vagal stimulation becomes ineffective, then the lead may be dislodged.

If the criteria for vagal stimulation 410 have been met, vagal stimulation may be delivered to the patient 412. Delivery of vagal stimulation 412 may be substantially similar to the delivery of vagal stimulation 110 described herein with reference to FIG. 3.

After and/or during the delivery of vagal stimulation 412, the method 400 may include evaluating the performance 414 of the patient's physiological parameters in response to the vagal stimulation. For example, evaluating the performance 414 may include determining whether there has been any cardiac response to the vagal stimulation, whether there has been a VT/VF detected during the vagal stimulation, whether any other new arrhythmias have been caused by the vagal stimulation, whether there has been any hemodynamic deterioration, whether the heart rate has been lowered, or whether a pre-defined low rate has been reached.

In at least one embodiment, the performance evaluation process 414 may include monitoring physiological parameters of a patient (e.g., the electrical activity of the patient's heart) and analyzing the monitored physiological parameters for termination criteria. Analyzing the monitored physiological parameters may include determining whether the interval between the R-waves of the electrical activity of the patient's heart has increased, determining whether the interval between the P-waves and QRS complexes of the electrical activity of the patient's heart has increased, and determining whether the electrical activity of the patient's heart indicates a ventricular arrhythmia. If the intervals between the R-waves of the electrical activity of the patient's heart has not increased (e.g., in response to the vagal stimulation), if the intervals between the P-waves and the QRS complexes of the electrical activity of the patient's heart has not increased (e.g., in response to the vagal stimulation), or if the electrical activity of the patient's heart indicates ventricular arrhythmia, the performance evaluation process 414 may lead to a termination of the delivery of electrical stimulation to the patient's vagus nerve 412 (e.g., the method 400 will return to data collection 402).

Further, the method 400 may include a clock or time period expiration determination 416. If the clock has expired, the method 400 will return to data collection 402. If the clock has not expired, the method 400 will return to determining if the patient meets the criteria for vagal stimulation 410. In other words, vagal stimulation may be given a chance to correct the heart condition, but if it does not correct it within a certain time period, then such vagal stimulation will be terminated. The time period for the clock may be about 10 seconds to several minutes (e.g., 3 minutes), or about 10 heart beats to about 200 heart beats.

Figure 7:
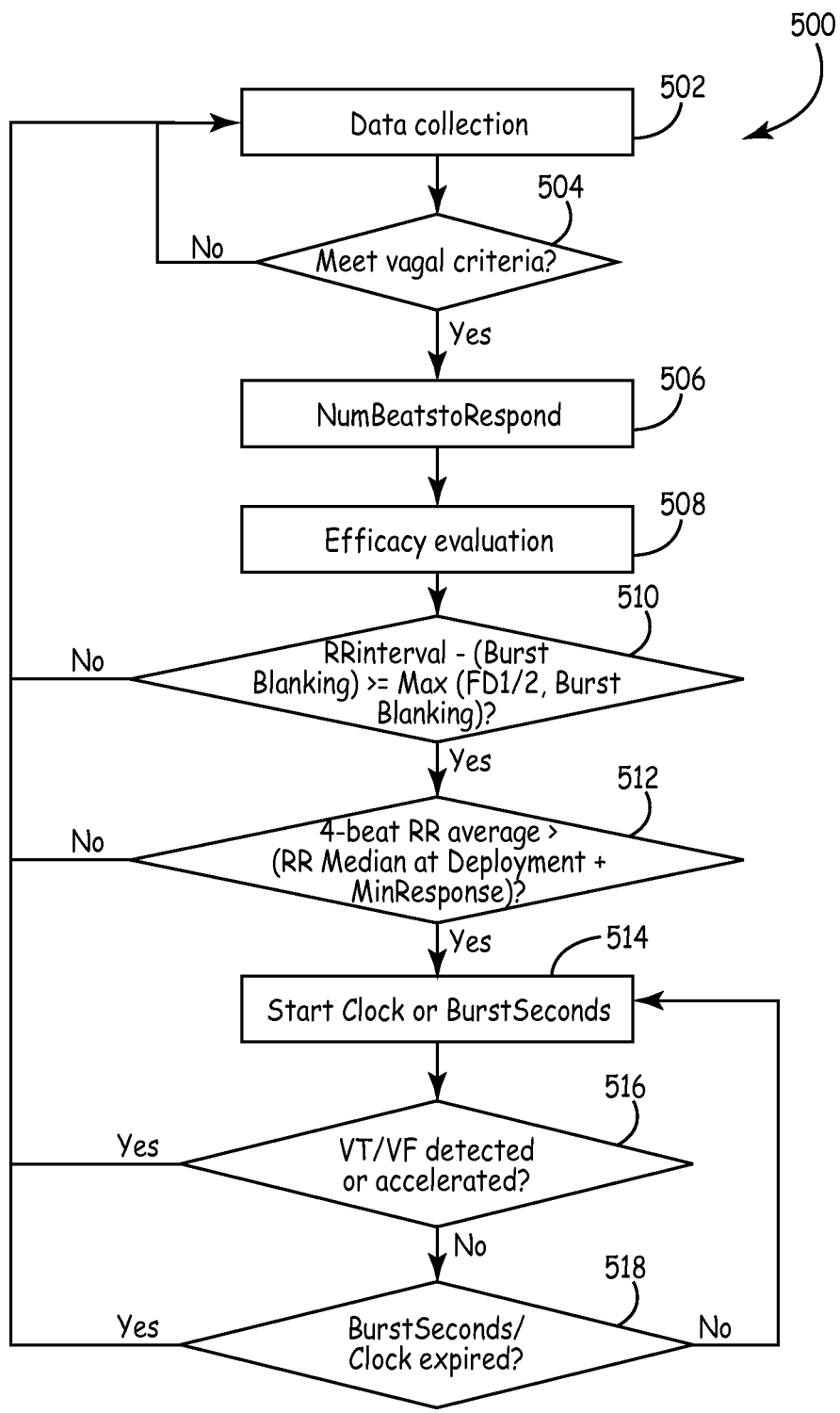
FIG. 7 is a flow chart of another exemplary method of delivering vagal stimulation and evaluating termination criteria.

FIG. 7 is a flow chart of another exemplary method 500 associated with the delivery of vagal stimulation and evaluation of vagal stimulation criteria/termination criteria. The method 500 includes a data collection process 502, which may be substantially similar to data collection process 102 described herein with reference to FIG. 3. If a cardiac condition is detected that may be treated by vagal stimulation, the method 500 may proceed to determine if the patient meets certain criteria for vagal stimulation 504, and if the patient's meets the criteria, vagal stimulation may be delivered to the patient (not shown). The criteria for vagal stimulation process 504 may be similar to the other criteria for vagal stimulation.

In certain situations, the V-V and/or A-V interval may not increase for several heart beats after delivering vagal stimulation, which may indicate that the vagal stimulation is ineffective. In these situations, a real VT/VF may be occurring and if so, appropriate ICD therapy should be activated. The expected response time after delivering vagal stimulation (e.g., for a V-V or A-V interval to begin to increase) may be about 5 heart beats. As such, the method 500 includes a delay for a NumBeatstoRespond period 506, which, e.g., may be the expected response time following a burst of vagal stimulation. The NumBeatstoRespond period 506 may be a selectable value representing the number of heart beats the method 500 should wait before evaluating the efficacy of the vagal stimulation 508. For example, the NumBeatstoRespond period 506 may be about 3 heart beats to about 8 heart beats. In at least one embodiment, the NumBeatstoRespond period 506 is about 5 heartbeats. Further, in at least another embodiment, the period 506 may be a selected time period (e.g., about 1 second to about 2 seconds).

After the NumBeatstoRespond period 506 has elapsed, the method 500 may evaluate the efficacy 508 of the vagal stimulation. Evaluating the efficacy 508 of the vagal stimulation includes processes substantially similar to evaluating the performance 414 of the patient's physiological parameters in response to the vagal stimulation described herein with reference to FIG. 6.

At least one additional process of evaluating the efficacy of the vagal stimulation may include comparing the R-R interval minus a burst blanking period (e.g., the burst blanking period may equal 30 ms plus the product of the number of burst pulses multiplied by 20 ms) to a max Fibrillation Detection Interval (FDI) (e.g., about 180 beats per minute, or about 330 ms) divided by two (e.g., such that a blanking period greater than 50% of the sensing window may be achieved) 510. If the R-R interval minus a burst blanking period is less than the maximum FDI divided by two, then the vagal stimulation may be ineffective, and the method 500 may deactivate any vagal stimulation and return to data collection 502.

Further, at least another additional process of evaluating the efficacy of the vagal stimulation may include comparing a four heart beat R-R interval average (e.g., the average R-R interval over any number of heart beats) to the R-R interval median observed at deployment (e.g., where vagal stimulation therapy is applied) plus a selected minimum response time 512. The minimum response time may be between about 100 ms and about 250 ms (e.g., about 100 ms, about 150 ms, about 200 ms, about 250 ms, etc.). If the four heart beat R-R interval average is less than the R-R interval median observed at deployment plus the minimum response time, the vagal stimulation may be ineffective, and the method 500 may deactivate any vagal stimulation and return to data collection 502.

Still further, at least another additional process of evaluating the efficacy of the vagal stimulation may include comparing each R-R interval to the R-R interval median observed at deployment (e.g., where vagal stimulation therapy is applied) plus a selected minimum response time. If any R-R interval is less than the R-R interval median observed at deployment plus the minimum response time, the vagal stimulation may be ineffective, and the method 500 may deactivate any vagal stimulation and return to data collection 502.

After the efficacy and/or termination criteria have been evaluated (e.g., such as using processes described in processes 508, 510, 512), a clock (e.g., BurstSeconds) 514 may be started. For example, the clock may run for about 30 or 45 seconds during which vagal stimulation may be active. Further, for example, the clock 514 may run for about 10 seconds to about 2 minutes. After the clock has expired 518, the method 500 may return to data collection 502. In other words, vagal stimulation may be given a chance to correct the heart condition, but if it does not correct it within a certain time period, then such vagal stimulation will be terminated.

A new VT/VF may occur after or during vagal stimulation (e.g., a VT/VF is detected or VT/VF is accelerated) 516. In this case, the vagal stimulation should be deactivated and ICD therapy should be delivered to the patient. For example, if at any time a VT/VF is detected or accelerated 516, the method 500 should return to data collection 502 and any ongoing vagal stimulation should be deactivated. In least one embodiment, if the vagal stimulation is terminated or deactivated for any reason other than the clock expiration 518, then the method 500 may prevent re-deployment of any vagal stimulation for a selected time period, e.g., 30 seconds. Further, sensing of VT/VF during burst pacing (e.g., vagal stimulation) should not be delayed such as the sensing falls outside of the burst window. As such, sensing to detect a VT/VF or acceleration of a VT/VF thereof should continue uninterrupted during vagal stimulation.

Figure 8:
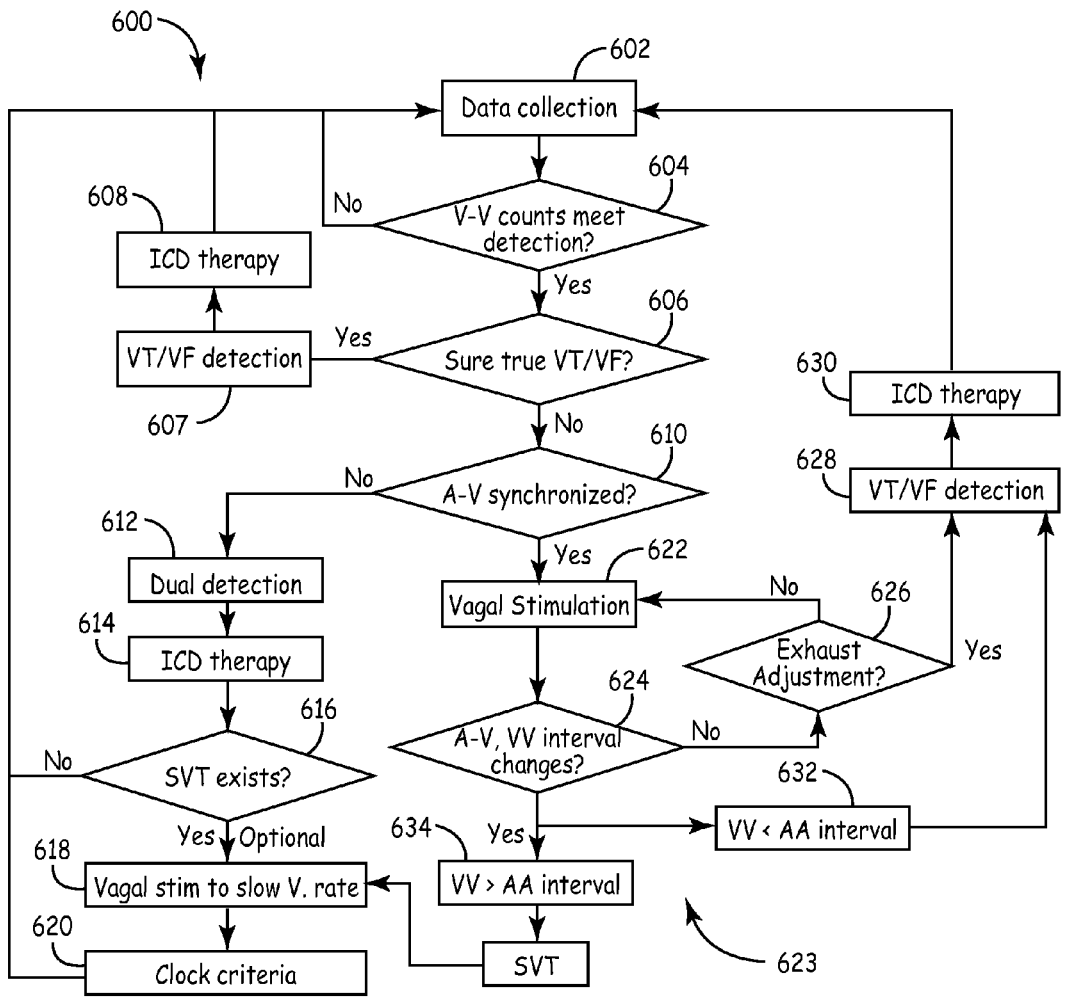
FIG. 8 is a flow chart of an exemplary method of treating various cardiac conditions.

FIG. 8 is a flow chart of another exemplary method 600 of treating heart conditions using vagal stimulation. The method 600 includes a data collection process 602, which may be substantially similar to data collection process 102 described herein with reference to FIG. 3. Periodically or concurrently with the data collection 602, the method 600 includes a V-V count detection process 604.

In at least one embodiment, the V-V count detection 604 includes comparing a VT/VF count to a selected value (e.g., 20). If the VT/VF count is less than the selected value, then the method 600 returns to data collection 602. The VT/VF count is the sum of a VT counter and a VF counter. If the VT/VF count is greater than the selected value, then the method 600 may proceed to determine whether a "sure true" VT/VF exists 606.

The VT counter keeps track of how many consecutive R-R intervals are less than the Tachycardia Detection Interval (TDI) (e.g., the VT counter is increased by one for each consecutive R-R interval that is less than the TDI). The tachycardia detection interval may be about 200 ms to about 600 ms. Further, the VT counter is reset to zero if a R-R interval is greater than the TDI.

The VF counter keeps track of how many R-R intervals out of a selected number of intervals (e.g., 24 intervals) are less than the Fibrillation Detection Interval (FDI) (e.g., the VF counter is the number of R-R intervals over the last 24 intervals that were less than the FDI).

In at least another embodiment, the V-V count detection 604 may include comparing the intervals between successive R-waves to a programmed FDI. For example, if a predetermined number or amount of R-R intervals (e.g., 18 intervals) out of a selected number or amount of R-R intervals (e.g., 24 intervals) are not less than the tachycardia detection interval (e.g., about 300 ms), the method 600 returns to data collection 602. Further, for example, if a predetermined number or amount of R-R intervals over a selected period of time (e.g., 5 seconds or 12 to 16 R-wave consecutive intervals) are not less than the tachycardia detection interval, the method 600 returns to data collection 602. In at least one embodiment, if 18 R-R intervals out of 24 of R-wave intervals or if 18 R-wave intervals over of 5 seconds are not less than the tachycardia detection interval, the method 600 returns to data collection 602.

If the V-V count process indicates a cardiac event (e.g., if the VT/VF counter is greater than a selected value), then the method 600 next determines whether a "sure true" VT/VF exists 606. In one or more embodiments, a "sure true" VT/VF may be detected if it is determined that the ventricular rate exceeds approximately 150 beats per minute and such ventricular rate lasts for more than 10 heart beats. In at least another embodiment, determining that a "sure true" VT/VF exists may include determining whether the QRS morphology is indicative of normal sinus rhythm and/or determining whether the timing of atrial and ventricular activations is indicative of sinus tachycardia or supraventricular tachycardia (e.g., if the QRS morphology is not indicative of normal sinus rhythm and/or whether the timing of atrial and ventricular activations is not indicative of sinus tachycardia or supraventricular tachycardia, then a "sure true" VT/VF may exist).

If a "sure true" VT/VF is detected 607, the method 600 may proceed to deliver ICD therapy 608 (e.g., ventricular pacing). ICD therapy 608 may be substantially similar to the ICD therapy 117 described herein with reference to FIG. 3. After the ICD therapy 608 has completed treating the VT/VF, the method 600 may return to data collection 602.

If a "sure true" VT/VF is not detected, the method 600 may analyze the A-V synchronization 610. In at least one embodiment, analyzing the A-V synchronization 610 includes an analysis of the synchrony between atrial events (e.g., P-waves) and ventricular events (e.g., R-waves). For example, if the R-waves that are similar to R-waves during sinus rhythm are synchronized to the P-waves in a 1:1 or other less frequent ratio, the ventricular tachycardia intervals may be the result of a SVT. The test for A-V synchrony may include verifying an interval pattern consistent with A-V conduction such as an A-V-A-V pattern, A-A-V-A-A-V pattern, etc. Further, the test for AV synchrony may additionally or alternatively include measuring P-R intervals (e.g., the intervals between sensed atrial events and successive ventricular events). If the sensed ventricular events occur within a predetermined interval of a preceding atrial event, the ventricular event is determined to be an atrial conducted event evidencing A-V synchrony. A regular pattern of A-V synchrony as supported by an A-V pattern and/or P-R intervals during the occurrence of VT intervals would lead to a detection of A-V synchrony.

If A-V synchrony 610 is not present, a dual tachycardia is detected 612 and appropriate ICD therapies are delivered 614 in response to the dual tachycardia detection. Although not shown in FIG. 8, the method 600 may include further processes to confirm dual tachycardia detection. For example, such processes may include analyzing additional information such as, e.g., QRS morphology to determine that a dual tachycardia exists.

Appropriate ICD therapy 614 may include ventricular therapy for treating the VT and an atrial therapy for treating the AT. Further, ICD therapy 614 may be substantially similar to the ICD therapy 117 described herein with reference to FIG. 3. After the ICD therapy 614 has completed treating the dual tachycardia, the method 600 may proceed to determining if a SVT exists 616. Methods of detecting and/or determining a SVT are described in, e.g., U.S. Pat. App. Pub. No. 2008/0269819 A1 to Zhou, which is incorporated herein by reference in its entirety.

If a SVT is not detected, the method 600 may return to data collection 602. If a SVT is detected, the method 600 may optionally deliver vagal stimulation 618 to treat the SVT (e.g., to slow the ventricular rate). Delivery of vagal stimulation 618 may be substantially similar to the delivery of vagal stimulation 110 described herein with reference to FIG. 3. Further, before, after, and/or during the delivery of vagal stimulation 618, vagal stimulation criteria, termination criteria, and/or clock criteria may be evaluated 620, which may includes processes similar to the processes 410, 414, and 416, respectively, described herein with respect to FIG. 6.

If A-V synchrony 610 is determined to be present (e.g., which may indicate that a VT/VF is unlikely present), vagal stimulation is delivered 622. Delivery of vagal stimulation 622 may be substantially similar to the delivery of vagal stimulation 110 described herein with reference to FIG. 3.

After and/or during the delivery of vagal stimulation 622, the method 600 may perform A-V/V-V interval change verification process 623 to determine if the vagal stimulation is effective in exciting neural tissue to, e.g., cause a parasympathetic response. A parasympathetic response may include one or more of a decrease in heart rate, an increase in A-V conduction time, a decrease in blood pressure, etc. In one embodiment, the verification process 623 includes measuring A-V intervals (i.e., the intervals between P-waves and QRS complexes) and comparing the A-V intervals measured after beginning vagal stimulation to A-V intervals measured prior to starting vagal stimulation 624, e.g., during the VT interval detection 604.

If no change in cardiac condition has been determined after and/or during the delivery of vagal stimulation 622 (e.g., no change in A-V intervals or V-V intervals), the method 600 may adjust the vagal stimulation 626. For example, the number of pulses included in a train of stimulating pulses may be adjusted (e.g., increased), the frequency of the pulse train may be adjusted (e.g., increased), and/or the amplitude of the stimulation pulses may be adjusted (e.g., increased). Further, if other electrodes are available for stimulating the vagus nerve, different electrodes may be selected for stimulating the vagus nerve. Still further, adjusting the vagal stimulation 626 may includes processes similar to portions of the vagal stimulation adjustment method 300 described herein with respect to FIG. 5.

If, however, each and every parameter of vagal stimulation has been adjusted without yielding any effective results (e.g., an effective result may be an increase in the monitored A-V intervals or V-V intervals), then the method 600 may determine that the adjustments have been exhausted 626 and proceed to determining that the cardiac event may be a VT/VF 628 (e.g., vagal stimulation may not be effective for particular tachyarrhythmias such as accessory or abnormal pathway tachyarrhythmias, i.e., not through the AV node), subsequently delivering ICD therapy 630, and, after treating the VT/VF with the ICD therapy, returning to data collection 602. ICD therapy 630 may be substantially similar to the ICD therapy 117 described herein with reference to FIG. 3. For example, the method 600 may include a pre-determined (e.g., programmed on the IMD) set of adjustments to modify the vagal stimulation in an effort to yield effective results. If each of the pre-determined adjustments of the set of adjustments has been tried without any success (e.g., no effective results), then the adjustments may be exhausted.

In other words, the method 600 may deliver electrical stimulation to the patient's vagus nerve 622, adjust the electrical stimulation delivered to the patient's vagus nerve based on the analysis of the monitored physiological parameters 626, terminate the delivery of electrical stimulation to the patient's vagus nerve after exhausting the adjustments to the electrical stimulation delivered to the patient's vagus nerve. Thereafter, for example, ventricular arrhythmia therapy may be delivered to the patient's heart after terminating the delivery of electrical stimulation to the patient's vagus nerve 630.

Further, the vagal stimulation may be adjusted if the intervals between the R-waves within the electrical activity of the patient's heart have not changed in response to the delivery of electrical stimulation to the patient's vagus nerve, if the intervals between the P-waves and the QRS complexes within the electrical activity of the patient's heart have not changed in response to the delivery of electrical stimulation to the patient's vagus nerve, and/or if the morphology of the R-waves of the electrical activity of the patient's heart has not changed in response to the delivery of electrical stimulation to the patient's vagus nerve. At least in one embodiment, exhausting the adjustments to the electrical stimulation delivered to the patient's vagus nerve may include determining that the adjustments have not changed at least one of the intervals between the R-waves, the intervals between the P-waves and the QRS complexes, and the morphology of the R-waves of the electrical activity of the patient's heart.

If a change in cardiac condition has been determined 624 after and/or during the delivery of vagal stimulation 622, the method 600 may next determine if the V-V intervals are either greater than the A-A intervals 634 or less than the A-A intervals 632.

If the V-V intervals are less than the A-A intervals 632, then the method 600 may proceed to determining that the cardiac event may be a VT/VF 628, subsequently delivering ICD therapy 630, and, after treating the VT/VF with the ICD therapy, returning to data collection 602. If the V-V intervals are greater than the A-A intervals 634, then the tachycardia may be detected as a SVT, and the method 600 may proceed to deliver vagal stimulation 618 to treat the SVT as described herein.

Figure 9:
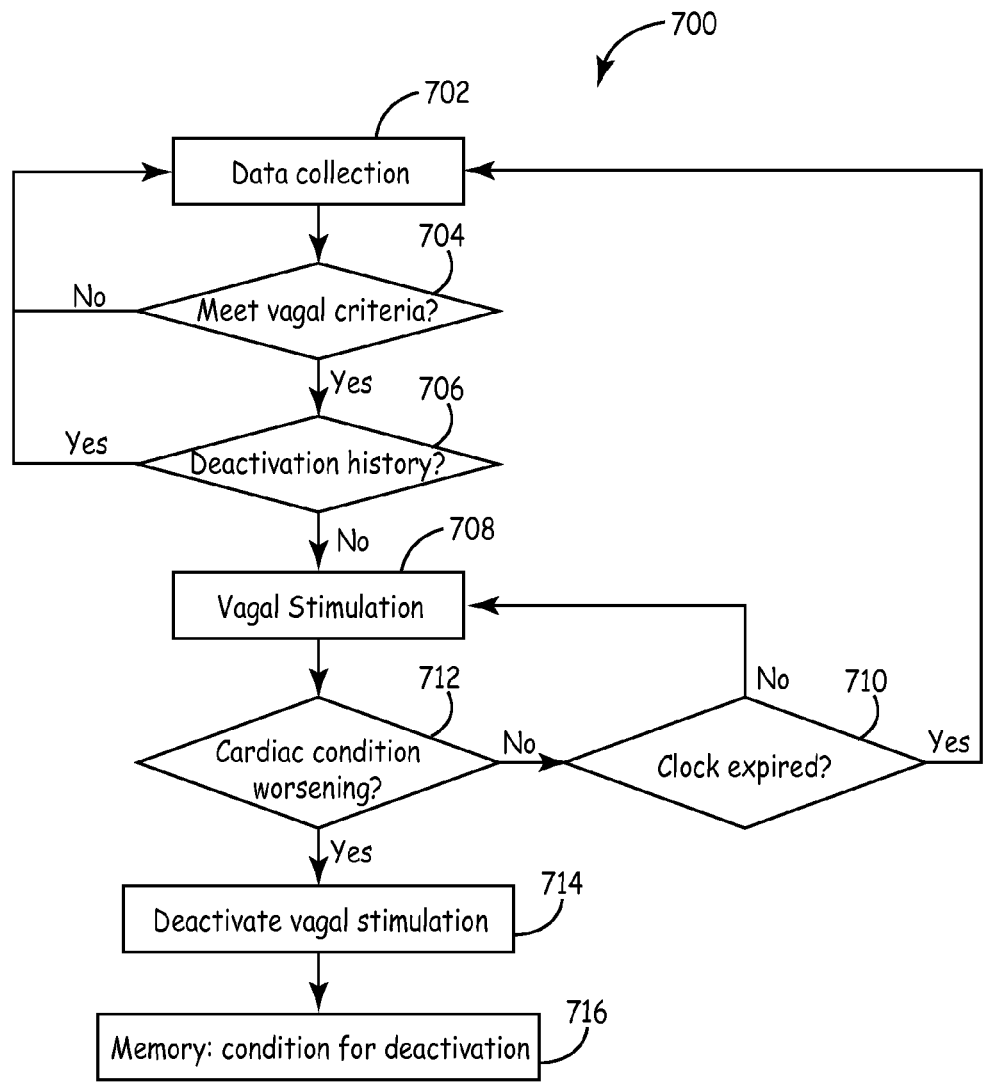
FIG. 9 is a flow chart of an exemplary method of preventing delivery of vagal stimulation based on deactivation history.

FIG. 9 is a flow chart of an exemplary method 700 of preventing delivery of vagal stimulation based on deactivation history. The method 700 includes a data collection process 702, which may be substantially similar to data collection process 102 described herein with reference to FIG. 3. If a cardiac condition is detected that may be treated by vagal stimulation, the method 600 may proceed to determining if the patient meets the criteria for vagal stimulation 704 (e.g., which may include processes relating to the criteria for vagal stimulation as described herein with reference to FIG. 6). If the patient does not meet the criteria for vagal stimulation, the method 700 may return to data collection 702.

Method 700 includes an additional criteria process with respect to deactivation history. For instance, if the patient meets the criteria for vagal stimulation in process 704, the method 700 may analyze the deactivation history 706 to determine either if a particular type of vagal stimulation (e.g., vagal stimulation delivered at a specific set of parameters) had been previously ineffective in treating the patient or if vagal stimulation had been previously ineffective in treating the patient's presently monitored physiological parameters. In other words, the method 700 may analyze the deactivation history (e.g., stored parameters of a particular type of vagal stimulation that have been determined to be ineffective in treating the patient's cardiac conditions, stored physiological parameters of the patient that have been determined to not be effectively treatable by vagal stimulation, etc.) to determine if the method 700 may deliver vagal stimulation to effectively treat the patient's cardiac condition.

If it is determined that vagal stimulation will not effectively treat the patient's cardiac condition in view of the deactivation history, the method 700 may return to data collection 702. If it is determined that vagal stimulation may be effective in treating the patient's cardiac condition, the method 700 may proceed to delivering vagal stimulation 708. Delivery of vagal stimulation 708 may be substantially similar to the delivery of vagal stimulation 110 described herein with reference to FIG. 3.

Periodically or concurrently with the delivery of vagal stimulation 708, the method 700 may evaluate if a selected period of time has expired 710 (e.g., measured either in time or heart beats). If the selected period of time has expired, the method 700 may return to the data collection 702. In other words, vagal stimulation may be given a chance to correct the heart condition, but if it does not correct the heart condition within a certain time period, then such vagal stimulation will be terminated.

Further, periodically or concurrently with the delivery of vagal stimulation 708, the method 700 may determine if the patient's cardiac condition is worsening 712, e.g., using the patient's monitored physiological parameters. The patient's cardiac condition may be worsening if it is determined that the patient is undergoing an AF and/or a VT/VF, if it is determined that the patient's heart is mechanically functionally deteriorating, and/or if the patient is undergoing chest pain and/or syncope (e.g., using a hemodynamic sensor to predict syncope). In at least one embodiment, determining whether the patient's cardiac condition is worsening includes comparing the patient's R-R interval to the patient's R-R interval before delivering vagal stimulation. Further, in at least one embodiment, a patient may manually deactivate the vagal stimulation using telemetry, etc. after, e.g., experiencing chest pain, thereby signaling that the patient's cardiac condition is worsening.

If the patient's cardiac condition is determined to be worsening (e.g., if the patient's present R-R interval is less that the patient's R-R interval before delivering vagal stimulation), the delivery of vagal stimulation may be terminated 714 (and the method 700 may return to data collection 702) and the conditions for deactivation may be stored 716 (e.g., in the memory of an IMD). For example, conditions for deactivation may include the monitored physiological parameters of the patient recorded before the delivery of the vagal stimulation (e.g., because such monitored physiological parameters of the patient indicate a cardiac condition that was unsuccessfully treated by vagal stimulation). Further, for example, conditions for deactivation may include the parameters of the vagal stimulation delivered to the patient (e.g., because such vagal stimulation was ineffective in treating the patient). Still further, conditions for deactivation may include both the monitored physiological parameters of the patient recorded before the delivery of the vagal stimulation and the parameters of the vagal stimulation delivered to the patient. As such, when the method 700 analyzes the deactivation history 706 to determine if the method 700 may deliver vagal stimulation to effectively treat the patient's cardiac condition, the deactivation history will include the newly stored conditions for deactivation, which may be used, at a later time, to prevent the delivery of vagal stimulation (e.g., if the vagal stimulation is ineffective in treating the patient's particular cardiac condition, or if the particular vagal stimulation is ineffective in treating the patient at all)

For example, if bursts of 15 pulses of vagal stimulation at 3 volts have previously been determined to be ineffective in treating a cardiac condition of the patient, the method 700 may prevent delivery of bursts of 15 pulses of vagal stimulation at 3 volts in the future. Further, for example, if a particular cardiac condition has previously been determined as not being effectively treatable by any vagal stimulation, the method 700 may prevent the delivery of vagal stimulation if the same particular cardiac condition is detected (e.g., a certain heart rate and hemodynamic pressure).

In other words, method 700 includes delivering electrical stimulation to the patient's vagus nerve 708, analyzing the monitored physiological parameters after delivering electrical stimulation to the patient's vagus nerve and determining if the patient's cardiac condition is worsening after delivering electrical stimulation to the patient's vagus nerve 712. The delivery of electrical stimulation to the patient's vagus nerve is terminated if the patient's cardiac condition is worsening 714. Further, the parameters of the electrical stimulation delivered to the patient's vagus nerve associated with the worsening of the patient's cardiac condition are stored 716, and at a later time, delivery of the electrical stimulation to the patient's vagus nerve is prevented at the previously stored parameters associated with the worsening of the patient's cardiac condition 706.

Figure 10:
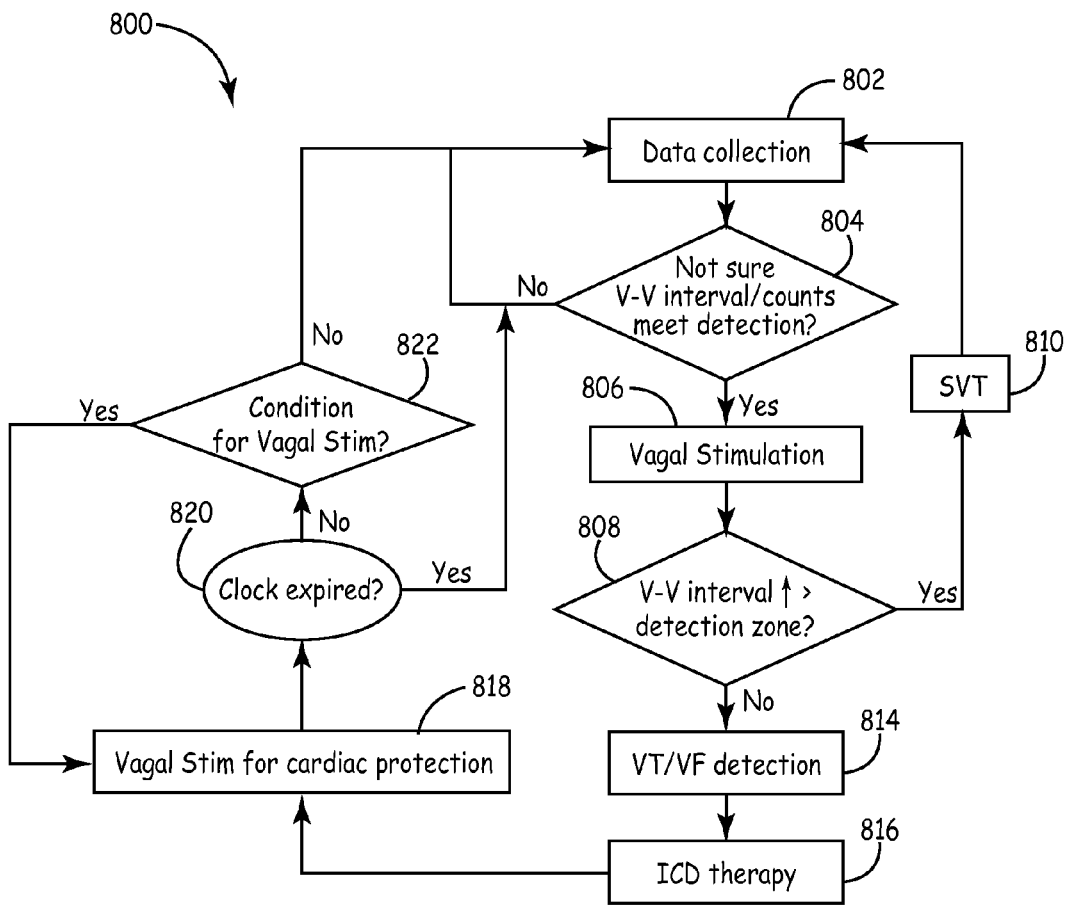
FIG. 10 is a flow chart of an exemplary method of treating various cardiac conditions and delivering vagal stimulation for protection against recurring arrhythmias.

Vagal stimulation may also be useful in the prevention (e.g., the reduction of risk or the severity) of recurring arrhythmias (e.g., a VT/VF) and/or myocardial infarction/ischemia. FIG. 10 is a flow chart of an exemplary method 800 of treating various cardiac conditions and delivering vagal stimulation for protection against recurring arrhythmias. The method 800 includes a data collection process 802, which may be substantially similar to data collection process 102 described herein with reference to FIG. 3.

Periodically or concurrently with the data collection 802, the method 800 executes a V-V interval/count detection process 804, which may be similar to the V-V interval/count detection process 604 described herein with reference to FIG. 8. If the V-V interval/count detection does not indicate an arrhythmia, then the method 800 returns to data collection 802.

If the V-V interval/count detection indicates an arrhythmia, then the method 800 delivers vagal stimulation 806 and monitors the V-V interval 808 to, e.g., determine if the arrhythmia is a VT/VF or a SVT. If the V-V interval is increased in response to the vagal stimulation, it may be determined that the arrhythmia is a SVT 810 and more vagal stimulation may be delivered 806 and optionally adjusted 812 accordingly to treat the SVT (e.g., the V-V interval may be intermittently determined and the parameters of the vagal stimulation may be adjusted to increase the V-V interval until a clock expires similar to portions of the vagal stimulation adjustment method 300 described herein with reference to FIG. 5).

If the V-V interval is not increased in response to the vagal stimulation, it may be determined that the arrhythmia is a VT/VF 814 and ICD therapy 816 may be delivered to the patient to treat the VT/VF. ICD therapy 816 may be substantially similar to the ICD therapy 117 described herein with reference to FIG. 3.

After the VT/VF has been treated with the ICD therapy (e.g., to obtain a healthy cardiac rhythm identified by one or more predetermined parameters), the method 800 may include delivering vagal stimulation for cardiac protection 818 (e.g., for prevention against future arrhythmias). The vagal stimulation for cardiac protection 818 may assist the patient in maintaining a healthy cardiac rhythm, e.g., through boosting the parasympathetic component of the vagus nerve. Further, after and/or during the delivery of vagal stimulation for cardiac protection 818, conditions for vagal stimulation 822 and/or clock criteria 820 (e.g. time period criteria) may be evaluated, which may include processes similar to the processes 410/414 and 416, respectively, of method 400 described herein with respect to FIG. 6.

In at least one embodiment, the conditions for vagal stimulation 822 may include determining whether the vagal stimulation is producing any pro-arrhythmic effects, whether the patient's cardiac function is deteriorating, etc. If either the clock expires 820 (e.g., after a selected time has elapsed) or if it is determined from the analysis of the conditions 822 for vagal stimulation to terminate the vagal stimulation, the method 800 may return to data collection 802.

In other words, the method 800 includes monitoring physiological parameters of a patient (including, e.g., the electrical activity of the patient's heart) 802, analyzing the monitored physiological parameters for physiological parameters indicative of a ventricular arrhythmia 804, 808, and delivering cardiac therapy to treat a ventricular arrhythmia if the physiological parameters of the patient indicate a ventricular arrhythmia 814, 816. Electrical stimulation may be delivered to the patient's vagus nerve after the ventricular arrhythmia has been treated (e.g., a regular rhythm is achieved) to prevent further ventricular arrhythmias from recurring 818.

Although methods have been discussed herein with respect to treatment of VT/VF and SVT, such methods may be used to treat many other cardiac conditions such as, e.g., acute myocardial infarction/ischemia. When the heart encounters an insult like ischemia or faces long-term failure, the organs of the body may respond by demanding increased cardiac output. The heart, in turn, may respond to these demands as best as it can. To reduce stress on the heart in case of a compromised heart as with angina pectoris (e.g., stable or chronic) and/or heart attack, vagal stimulation may be delivered to assist the heart. For example, vagal stimulation may be delivered in response to high HR, ST segment changes, or other indications of cardiac insult.

To prevent an irregular rhythm in the ventricle, the vagal stimulation may be titrated to achieve a desired effect without AV block, or strong vagal stimulation may be combined with ventricular demand (WI, DDD, etc.) pacing. Further, for example, vagal stimulation may be delivered in case of compromised hemodynamics due to pump failure. Still further, in case of mitral stenosis, one could extend the filling phase if above a certain atrial rate by increasing A-V delays using vagal stimulation.

Vagal stimulation delivered near the A-V node generally blocks the A-V conduction thereby reducing ventricular rate. Vagal stimulation delivered near the sinus node generally directly reduces the intrinsic heart rate. A reduction in ventricular rate and/or intrinsic heart rate may decrease the workload of the heart during a myocardial infarction/ischemia, and thus, reduce the oxygen demand in an ischemia situation.

Further, abnormal automatic nervous activities, such as increased sympathetic surge, imbalance between parasympathetic and sympathetic activity, etc. may contribute to the rupture of plaque leading to acute myocardial infarction (AMI) and larger infarction sizes due to an increase in cardiac workload at the time of oxygen supply reduction (further, oxygen supply reduction may lead to necrosis of cardiac tissue). Excitation of the cardiac parasympathetic neurons or stimulation of the parasympathetic fibers of the vagus nerve may reduce over-excitation of the cardiac sympathetic nerves (e.g., which decreases the heart rate, and hence oxygen demand) and/or may increase cholinergic anti-inflammatory effect. As such, vagal stimulation may be used to prevent AMI and/or reduce infarction size if AMI occurs, via the mechanisms of reduction of work load (e.g., through a slower heart rate) and anti-inflammatory effects. Therefore, vagal stimulation delivered to intracardiac parasympathetic neurons (e.g., the fat pads near the SVC and IVC, the base of the right ventricle, the septal region of the right atrium, vagal bundle, the spinal cord at the cervical and thoracic levels, etc.) may assist in treating and/or preventing AMI and infarction size. In other words, electrical stimulation of the vagus nerve may be therapeutic, e.g., to treat an AMI upon detection thereof, and preventative, e.g., to lower the risk of AMI (and/or the effects once an AMI occurs).

Figure 11:
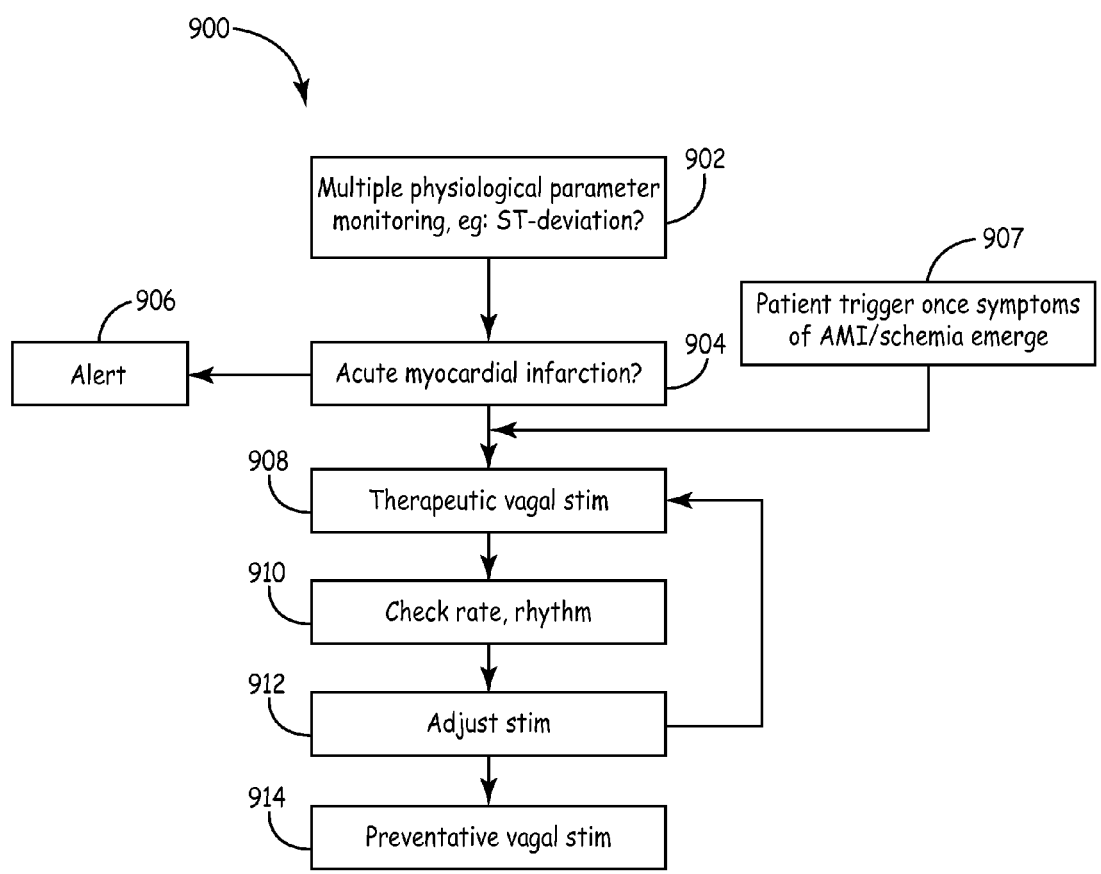
FIG. 11 is a flow chart of an exemplary method of treating acute myocardial ischemia/infarction using vagal stimulation.

FIG. 11 is a flow chart of an exemplary method of treating acute myocardial infarction/ischemia using vagal stimulation. The method 900 includes monitoring multiple physiological parameters (e.g., ST segment), which may be substantially similar to data collection process 102 described herein with reference to FIG. 3.

Using the physiological conditions monitored during data collection 902, the method 900 may determine whether the monitored physiological conditions indicate acute myocardial infarction 904. Monitored physiological conditions indicative of acute myocardial infarction/ischemia may include ST elevation/depression, heart sound changes, T-wave changes, QRS vectors/waveforms, QRS onset slope, pressure changes, intrathoracic impedance, ion concentrations, local temperatures, coronary sinus blood return, selected biomarkers, and/or any combination of thereof.

If it is determined that the monitored physiological conditions indicate acute myocardial infarction/ischemia, the method 900 may deliver (e.g., through telemetry, etc.) an alert 906 to, e.g., the patient, monitoring apparatus, etc., indicating that the patient is undergoing acute myocardial infarction/ischemia. For example, a ST-deviation (e.g., ST-deviation includes ST-elevations and ST-depressions) may indicate acute myocardial infarction due to, e.g., plaque rupture which has occluded the coronary artery. Further, the method 900 may include delivering therapeutic vagal stimulation 908 (i.e., electrical stimulation the patient's vagus nerve) to treat the acute myocardial infarction/ischemia, checking/analyzing the monitored physiological parameters 910 (e.g., heart rate, heart rhythm, etc.), and adjusting the vagal stimulation 912 based on the monitored physiological parameters. For example, the therapeutic vagal stimulation may be adjusted if the ST-deviation of the electrical activity of the patient's heart has not decreased. The delivery of therapeutic vagal stimulation 908 may be similar to the delivery of vagal stimulation 110 described herein with reference to FIG. 3. Further, checking/analyzing the monitored physiological parameters 910 and adjusting the vagal stimulation 912 may include processes similar to portions of the vagal stimulation adjustment method 300 described herein with reference to FIG. 5.

In at least one embodiment, therapeutic vagal stimulation may be delivered 908 until the physiological parameters of the patient (e.g., the electrical activity of the patient's heart) indicate that the progression of the AMI has ceased. In other words, the delivery of therapeutic vagal stimulation 908 may be terminated if the physiological parameters indicate cessation of the progression of the AMI. For example, if the ST-deviation of the electrical activity of the patient's heart has decreased, then the progression of the AMI may have ceased and the therapeutic vagal stimulation may be terminated.

Further, if the method 900 has not determined that the monitored physiological conditions indicate acute myocardial infarction/ischemia, a patient may trigger 907 the delivery of therapeutic vagal stimulation 910 if, e.g., the patient experiences one or more symptoms indicative of acute myocardial infarction/ischemia. In one or more embodiments, the patient may trigger 907 the delivery of therapeutic vagal stimulation through the use of telemetry, e.g., IMD telemetry circuitry 64, or telemetry module, as described herein within reference to FIG. 2.

Although method 900 describes the use of therapeutic vagal stimulation to treat a myocardial infarction after a myocardial infarction is detected, methods and devices disclosed herein may be used to prevent, or lower the risk of, future myocardial infarctions by enhancing the parasympathetic activity of the vagus nerve (e.g., to counter surges in sympathetic activity) with preventative vagal stimulation. Such AMI prevention methods using preventative vagal stimulation may be similar to the method 800 described herein with reference to FIG. 10 (which describes a method of delivering vagal stimulation for protection against future arrhythmias).

For example, as described herein, vagal stimulation may be used to reduce the A-V interval, A-A interval, and V-V interval, which it turn, may reduce the workload of the heart and may reduce the inflammatory response, e.g., which may lower the risk of future myocardial infarction/ischemia. In at least one embodiment, preventative vagal stimulation for the prevention of myocardial infarctions may be delivered periodically, e.g., one or more times a day with a selected duration and frequency. For example, preventative vagal stimulation may be delivered in the early morning to counter a surge of sympathetic activity, e.g., associated with a patient's body awakening. In other words, periods of preventative vagal stimulation may correspond to periods of increasing sympathetic activity, may be scheduled, and/or may be delivered upon detection of an AMI. Further, for example, preventative vagal stimulation may be delivered to a patient once an hour while the patient is awake to assist in lowering the risk of a myocardial infarction.

In at least one embodiment of a method for use in treating a patient with vagal stimulation to lower the risk of a myocardial infarction, the method may include monitoring physiological parameters of a patient including the electrical activity of the patient's heart and the electrical activity of the patient's vagus nerve and detecting conditions indicative of an increased risk of myocardial infarction (e.g., a ST-deviation, a selected number of ischemia episodes, ischemia burden, a selected number of arrhythmic beats over a selected time period, ST changes at rest, delta ST in conjunction with bradyarrhythmias, etc.) using the monitored physiological parameters. Further, in at least one embodiment, once a patient has experienced an AMI, then the preventative method may be invoked (e.g., an IMD may be implanted to deliver preventative vagal stimulation).

Such monitored physiological parameters may be analyzed. For example, the electrical activity of the patient's vagus nerve may be analyzed to determine if it indicates an increase in sympathetic activity. Upon at least one indication of an increase in sympathetic activity in the electrical activity of the patient's vagus nerve (e.g., monitored physiological parameters that indicate that the patient has awaken from sleep), the preventative method may deliver preventative electrical stimulation to the patient's vagus nerve to decrease at least one of the workload and inflammation of the patient's heart. In one or more embodiments, the delivery of preventative electrical stimulation to the patient's vagus nerve may be synchronized to blanking periods associated with the R-waves within the electrical activity of the patient's heart. Further, in one or more embodiments, the methods may further include adjusting the electrical stimulation delivered to the patient's vagus nerve based on the analysis of the monitored physiological parameters until the P-R intervals, A-A intervals, and/or V-V intervals within the electrical activity of the patient's heart have increased to a level that reduces the workload of the patient's heart.

Further, as shown in FIG. 11, after using therapeutic vagal stimulation treat a detected acute myocardial infarction, the method 900 may deliver preventative vagal stimulation 914 (e.g., periodically) to assist in lowering the risk of future myocardial infarctions (e.g., by decreasing workload, etc.).

To reduce AT/AF symptoms, the ventricular rate may be slowed down during AT/AF with vagal stimulation. Battery life, however, may be a limiting factor in delivering vagal stimulation for reducing AT/AF symptoms. As such, it may be advantageous for battery life to only deliver vagal stimulation to reduce AT/AF symptoms when certain sudden changes occur (e.g., observed changes in atrial rhythm or in ventricular rhythm).

Figure 12:
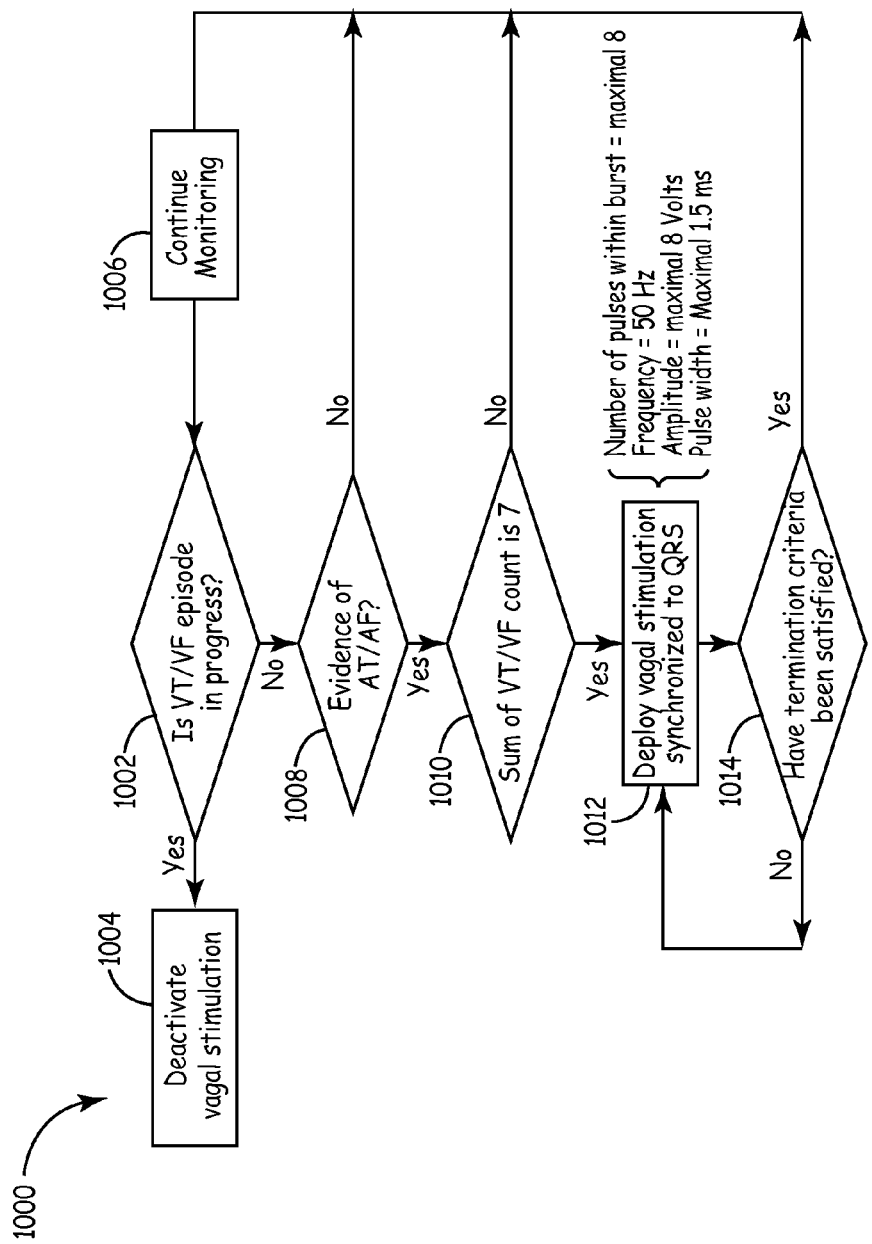
FIG. 12 is a flow chart of an exemplary method of delivering vagal stimulation during atrial tachycardia or fibrillation.

FIG. 12 is a flow chart of an exemplary method 1000 of delivering vagal stimulation during atrial tachycardia or fibrillation. The method 1000 includes determining if a VT/VF episode is in progress 1002. If a VT/VF is detected, the method 1000 deactivates any ongoing vagal stimulation.

If a VT/VF is not detected, the method 1000 may determine if an AT/AF is occurring 1008 (e.g., the method may analyze monitored physiological parameters of the patient for evidence indicative of AT/AF). For example, if the P-P interval median is less than the R-R interval median (e.g., over a certain time period) when the R-R interval median is greater than the fibrillation detection interval (FDI) and less than the tachycardia detection interval (TDI) or when the R-R interval median is less than the fibrillation detection interval (FDI), then an AT/AF may be occurring. Further, for example, if the sinus tachycardia counter (e.g., PR Logic Sinus Tach CRM counter) is less than 6 (or any other set number) (e.g., not sinus tachycardia), then an AT/AF may be occurring. Still further, for example, if the R-R interval median is smaller than a selected value (e.g., a programmable minimum) and is greater than or equal to the VagalStimMaxLimit (i.e., the largest median R-R interval where vagal stimulation should be applied which may be between about 300 ms and about 440 ms such as, e.g., about 300 ms, about 310 ms, about 360 ms, about 440 ms, etc.), then an AT/AF may be occurring. If it is determined that an AT/AF is not detected, the method 1000 may continue monitoring 1006 the physiological parameters of the patient (e.g., similar to the data collection 102 as described herein with reference to FIG. 3).

If an AT/AF is detected, the method 1000 may determine if the sum of the VT/VF count is greater or less than a selected value (e.g., 7) 1010, which may be similar to the V-V interval/count detection process 604 described herein with reference to FIG. 8. If the sum of the VT/VF count is less than 7, then the method 1000 may continue monitoring 1006 the physiological parameters of the patient.

If the VT/VF count is greater than 7, then the method 1000 proceeds to deploy vagal stimulation synchronized to the QRS complexes 1012 (e.g., in the blanking periods following the R-waves) of the electrical activity of the patient's heart. For example, the vagal stimulation 1012 may include bursts having up to a maximum of 8 pulses per burst, a frequency of about 50 hertz, an amplitude up to a maximum of about 8 volts, and a maximum pulse width of about 1.5 ms.

During and/or after the delivery of vagal stimulation 1012, the method 1000 may include determining whether termination criteria have been satisfied 1014, which may be similar to evaluating the performance 414 of the patient's physiological parameters in response to the vagal stimulation described herein with reference to FIG. 6. The termination criteria of process 1014 may include determining whether a minimum response occurs after a burst of vagal stimulation (e.g., whether the average of the previous 4 R-R intervals is greater than the R-R median interval at burst start plus 150 ms, etc.), whether a VT/VF is detected (which, as described herein, may be delayed due to the vagal stimulation, e.g., by a maximum of about 3 seconds), whether a shorter V-V interval is detected after the vagal stimulation (e.g., if the V-V interval is shorter than or equal to twice the burst blanking intervals of the vagal stimulation or if the V-V interval is less than the TDI or FDI), if the VT/VF count increases, and/or whether a specified burst time has been exceeded (e.g., 30 seconds).

If the termination criteria have not been satisfied, the method 1000 may continue to deliver vagal stimulation 1012. If the termination criteria have not been satisfied, the method 1000 will discontinue any ongoing vagal stimulation and continue to monitor 1006 the physiological parameters of the patient.

Epidemiological studies have shown that a high heart rate at rest is a risk factor for global cardiovascular mortality. A rapid heart rate is associated with a variety of prognostic factors indicative of worse heart conditions (e.g., hypoxemia, anemia, low physical training status). The link between a high resting heart rate and an increase in overall and cardiovascular mortality has, however, been shown to be independent of cardiac conditions that can contribute to an increase in the resting heart rate, and persists after adjustment for other classic variables (e.g., sex, arterial pressure, etc.). A heart failure patient experiences in case of lung edema an overcompensation, where the solution would be to lower the heart rate, and therefore, lower the burden on the heart. Atherosclerosis patients could benefit from reduced shear stress on the heart due to a lower heart rate.

As discussed herein, vagal stimulation, e.g., AV node stimulation, may be effective to reduce ventricular rate (in other words, to increase the R-R interval), especially if intrinsically conducted via the AV node in case of atrial tachyarrhythmias. Further, another way to reduce heart rate is through vagal stimulation near the sinus node to directly reduce the heart rate (e.g., within a defined range). The reduction of the ventricular rate or heart rate is dependent on the parameters of the vagal stimulation delivered to the patient. For example, the higher the energy (e.g., higher amplitude, higher the impulse duration, longer burst train frequency), the slower the ventricular rate (or, the longer the R-R interval). Such vagal stimulation techniques may be suitable for patients with atrial tachyarrhythmias and fast atrial events conducted in the ventricle.

Further, even if a patient is in sinus rhythm, the ventricular rate could be slower than the atrial rate during intrinsic conduction, which may be valuable for certain health conditions. Due to ongoing intrinsic conduction into both ventricular chambers (e.g., intrinsic conduction may indicate that the heart's electrical system is intact—in other words, the heart is capable of initiating a depolarization of cardiac cells and such depolarization is capable of spreading throughout the heart without assistance (e.g., without vagal stimulation)), there may be no worsening effects like right apical pacing, especially for patients with heart failure and no bundle branch block. As such, there may be no need to slow down the heart rhythm with drugs (e.g., beta blockers) and accelerate it again (e.g., DDDR/VVIR/DDIR pacing). Further, pacing modes (e.g., DDDR/VVIR/DDIR) may be switched only when the patient needs it, even in patients with healthy AV nodes.

Figure 13:
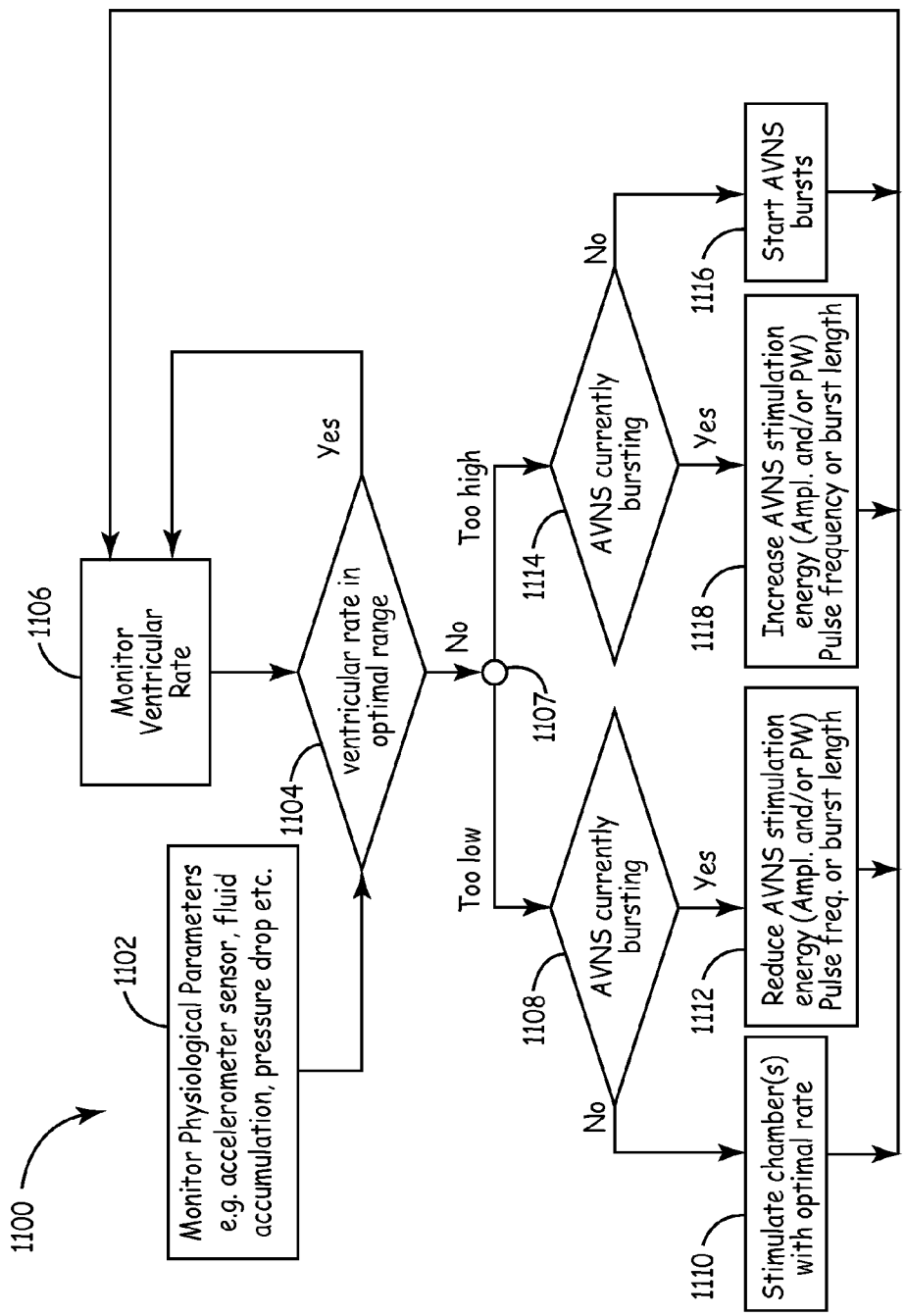
FIG. 13 is flow chart of another exemplary method of adjusting vagal stimulation for treating cardiac conditions.

FIG. 13 is a flow chart of another exemplary method 1100 of controlling ventricular rate by adjusting vagal stimulation. The method 1100 includes monitoring physiological parameters 1102 (e.g., accelerometer sensing, lung fluid status (e.g., using Medtronic Optivol), blood pressure (e.g., using hemodynamic sensors or optical sensors), pressure drop, ST segment analysis, etc.), which may be substantially similar to data collection process 102 described herein with reference to FIG. 3. Periodically and/or concurrently with the monitoring of physiological parameters 1102, the method 1100 includes determining if the ventricular rate (or, e.g., the V-V interval) is within an optimal range 1104. The optimal range may be variable depending on the activity level of the patient. For instance, the optimal range at rest may be different than optimal range during activity/exercise. As such, the lower bound and/or the upper bound of the optimal range may be changed based on monitored levels of activity and/or stress of the patient. In at least one embodiment, the optimal range for the ventricular rate may be about 50 beats per minute to about 100 beats per minute. If the ventricular rate is within the optimal range, the method 1100 continues monitoring the ventricular rate 1106 and either periodically or concurrently determines if the ventricular rate (or, e.g., the V-V interval) is within an optimal range 1104.

If the ventricular rate falls outside of the optimal range, the method 1100 may determine if the ventricular rate is either too low or too high 1107. In at least one embodiment, the ventricular rate may be determined to be too low if it is less than the lower bound of the optimal range and may be determined to be too high if it is higher than the upper bound of the optimal range (and, e.g., monitored levels of activity and/or stress do not indicate a need for the patient to have a higher rate).

If the ventricular rate is determined to be too low, the method 1100 checks whether AV node stimulation (e.g., vagal stimulation) is currently being delivered 1108 (e.g., bursted). If the AV node stimulation is not currently being delivered, then the method 1100 may deliver AV node stimulation 1110 at selected parameters based on the monitored one or more physiological parameters such as V-V intervals, pressure recordings, heart sound, lung sound, tissue perfusion, etc. thereby modifying the ventricular rate or heart rate within an optimal range. Although the normal heart rate range may be defined as about 60 beats per minute (bpm) to about 100 bpm, many heart failure patients may not be able to tolerate a high rate near 100 bpm. Therefore, an optimal rate should be defined as a rate that will not worsen cardiac condition and/or may improve cardiac function. For example, if a particular patient develops heart failure symptoms when their heart rate is 90 bpm, then using vagal stimulation to reduce their heart rate to 70 bpm would be considered as improving their cardiac function. If AV node stimulation (e.g., the AV node stimulation that was causing the AV node conduction block)

was currently being delivered, then the method 1100 may reduce the presently delivered AV node stimulation energy 1112 to, e.g., stimulation parameters less than those used in an AV node block, to allow the ventricular rate to increase and be within the optimal range. Methods of reducing the AV node stimulation energy 1112 may include reducing the amplitude, pulse widths, pulse frequency, and/or burst length (e.g., number of pulses per burst).

If the ventricular rate is determined to be too high, the method 1100 checks whether AV node stimulation (e.g., vagal stimulation) is currently being delivered, or bursted 1114. If the AV node stimulation is not currently being delivered, then the method 1100 may start delivering AV node stimulation bursts 1116 at selected parameters thereby stimulating the heart chambers to, e.g., achieve a ventricular rate within the optimal range. If the AV node stimulation was currently being delivered, then the method 1100 may increase the presently delivered AV node stimulation energy 1118 to allow the ventricular rate to decrease and be within the optimal range. Methods of increasing the AV node stimulation energy 1118 may include reducing the amplitude, pulse widths, pulse frequency, and/or burst length (e.g., number of pulses per burst). Further, in at least one embodiment, an alternative method of decreasing the heart rate into the optimal range may include intracardiac vagal stimulation near the sinus node.

After the AV node stimulation has either been started, increased, or decreased, the method 1100 may return to monitoring the ventricular rate 1106 and checking if the ventricular rate is within the optimal range 1104.

In other words, the method 1100 may continually loop and adjust the vagal stimulation, or AV node stimulation, to, e.g., increase or decrease the R-wave intervals of the electrical activity of a patient's heart. For example, the method may include increasing the electrical stimulation delivered to the patient's vagus nerve if the intervals between the R-waves within the electrical activity of the patient's heart are less than a first selected value (e.g., about 600 ms to about 700 ms) and decreasing the electrical stimulation if the intervals between the R-waves within the electrical activity of the patient's heart are greater than a second selected value (e.g., about 1000 ms to about 1200 ms). Increasing the electrical stimulation may include at least one of increasing the voltage of the electrical stimulation, increasing the frequency of the electrical stimulation, increasing the pulse width of each pulse of the electrical stimulation, and increasing the number of pulses per burst of pulses of the electrical stimulation. Likewise, decreasing the electrical stimulation may include at least one of decreasing the voltage of the electrical stimulation, decreasing the frequency of the electrical stimulation, decreasing the pulse width of each pulse of the electrical stimulation, and decreasing the number of pulses per burst of pulses of the electrical stimulation.

Cardiac contractility can be regulated via an internal mechanism of Starling Law, which means that an increase in preload (e.g., the pressure within the ventricle that stretches, or increases the volume, of the ventricle of the heart) will increase the contractility and vice versa. The preload is determined by the blood return to the ventricular chamber, and the blood return is generally determined by the sucking effect of ventricular relaxation followed by atrial contraction and a small amount of spontaneous blood flow. The interval of blood flow during atrial contraction and the spontaneous blood flow is related to the P-R interval. Thus, the preload, and thus contractility, of a patient's heart may be regulated using various methods and/or devices to, e.g., treat potential heart failure.

Figure 14:
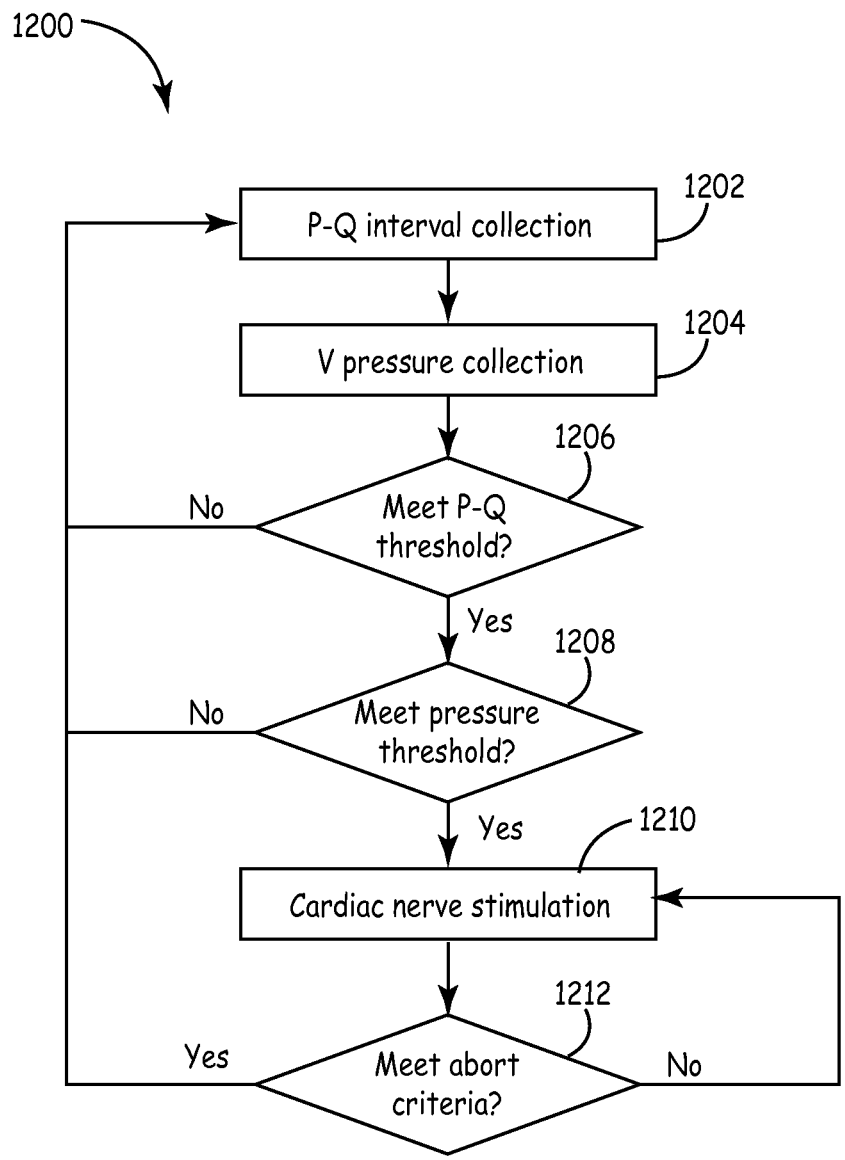
FIG. 14 is a flow chart of another exemplary method of delivering vagal stimulation.

FIG. 14 is a flow chart of an exemplary method 1200 of delivering vagal stimulation to, e.g., regulate preload (volume/pressure) of a patient's heart. The method 1200 includes P-Q interval collection 1202 in which the electrical activity (e.g., the P-Q intervals) of the patient's heart is monitored. The method 1200 further includes ventricular pressure collection 1204 in which the pressure of one or both the patient's ventricles is monitored. Although shown in FIG. 14 as being consecutive, processes 1202, 1204 may occur concurrently and/or in any order. Further, although not shown, the method 1200 may also monitor other various physiological parameters, which may be substantially similar to the data collection process 102 described herein with reference to FIG. 3.

Periodically and/or concurrently with P-Q interval collection 1202 and ventricular pressure collection 1204, the method 1200 includes determining if the P-Q intervals of the electrical activity of the patient's heart are less than a selected P-Q threshold value 1206 and determining if the ventricular pressure is greater than a selected ventricular pressure threshold value 1208.

The selected P-Q threshold value may be representative of the optimal P-Q interval for regulating preload and cardiac contractility to maintain health cardiac conditions. For example, the selected P-Q threshold value may be between about 180 ms to about 220 ms (e.g., depending on the cardiac health of the patient, the level of activity of the patient, etc.). If the monitored P-Q interval of the patient (e.g., an average P-Q interval over multiple cardiac cycles, etc.) is greater than the selected P-Q threshold value, then the method 1200 may return to P-Q interval collection 1202 and/or ventricular pressure collection 1204.

The selected ventricular pressure threshold value may be representative of the maximum ventricular pressure for regulating preload and cardiac contractility to maintain healthy cardiac conditions. For example, the selected ventricular pressure threshold value (e.g., of the end-diastolic pressure) may be between about 5 millimeters of mercury (mmHg) to about 20 mmHg (e.g., depending on the cardiac health of the patient, the level of activity of the patient, etc.). If the monitored ventricular pressure of the patient (e.g., sampled ventricular pressure of a period time, etc.) is less than the selected ventricular pressure threshold value, then the method 1200 may return to P-Q interval collection 1202 and/or ventricular pressure collection 1204.

If the monitored P-Q interval of the patient is less than the selected P-Q threshold value and the monitored ventricular pressure (e.g., the ventricular end-s diastolic pressure) of the patient is greater than the selected ventricular pressure threshold value, then the method 1200 may deliver cardiac nerve stimulation 1210 (e.g., vagal stimulation), which may be substantially similar to the delivery of vagal stimulation 110 described herein with reference to FIG. 3. Further, before, after, and/or during the cardiac nerve stimulation process 1210, criteria, termination criteria, and/or clock criteria may be evaluated 1212, which may be similar to the processes 410, 414, and 416 described herein with respect to FIG. 6. Further, the evaluation process 1212 may further include criteria based on ventricular pressure.

In other words, the method 1200 may monitor the electrical activity of a patient's heart, monitor the ventricular pressure of the patient's heart, and deliver electrical stimulation to the patient's vagus nerve based on the electrical activity and ventricular pressure of the patient's heart to, e.g., regulate preload and contractility. In at least one embodiment, the method may initiate the delivery of electrical stimulation to the patient's vagus nerve if an average of the P-R intervals of the electrical activity of the patient's is less than a selected P-R value and the ventricular pressure of the patient's heart is less than a selected pressure value.

Figure 15:
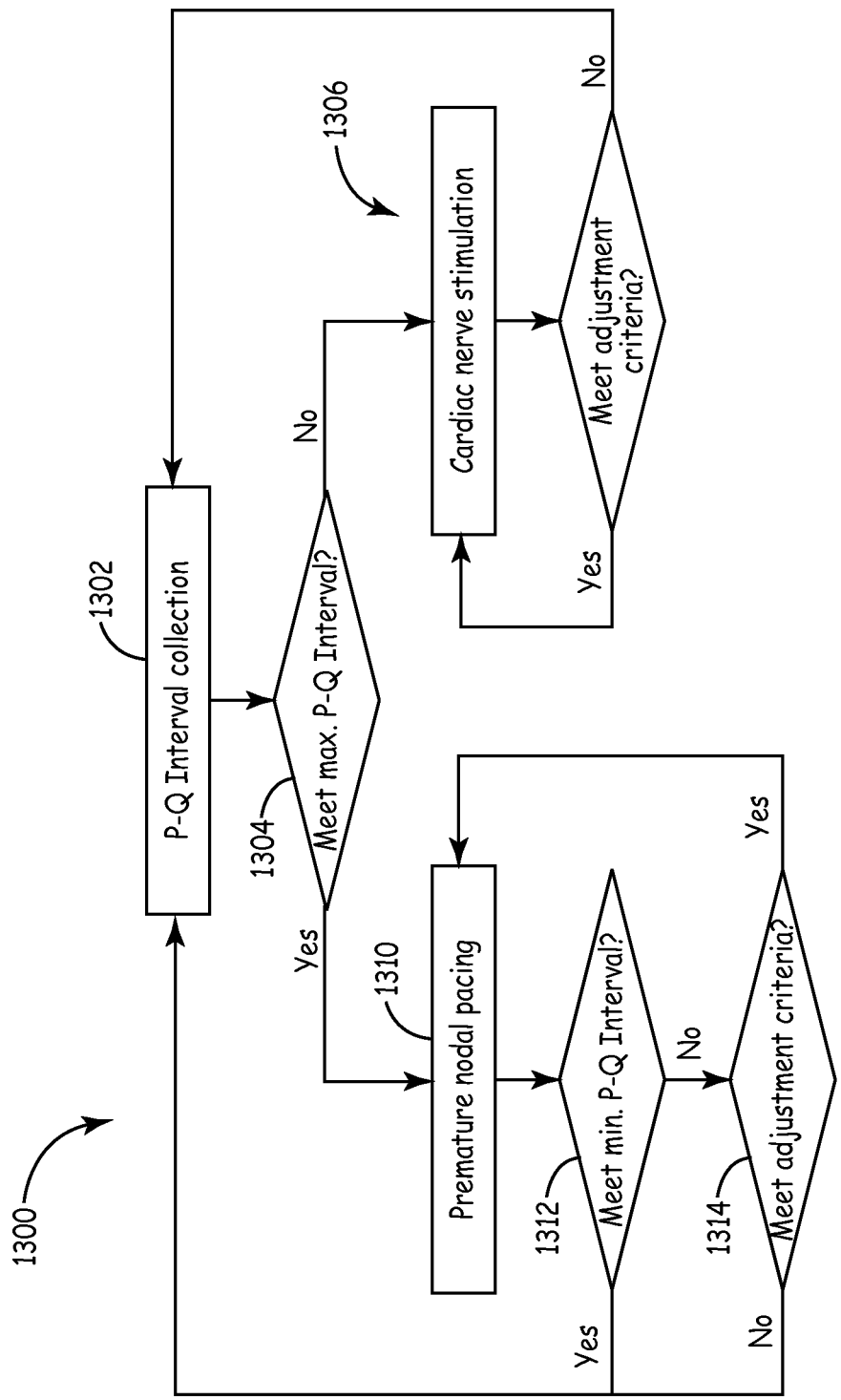
FIG. 15 is a flow chart of an exemplary method of delivering cardiac therapy.

FIG. 15 is a flow chart of another exemplary method 1300 of delivering cardiac therapy. The method 1300 includes P-Q interval collection 1302, which is substantially similar to process 1202 described herein with reference to FIG. 14.

Periodically and/or concurrently with P-Q interval collection 1302, the method 1300 includes determining if the monitored P-Q interval of the electrical activity of the patient's heart (e.g., average P-Q interval of a period time or number of cardiac cycles, etc.) are less than a selected maximum P-Q threshold value 1304. The selected maximum P-Q threshold value may be representative of the maximum P-Q interval indicative of improper preload and contractility of the heart, cardiac arrest, etc. For example, the selected maximum P-Q threshold value may be between about 200 ms to about 250 ms (e.g., depending on the cardiac health of the patient, the level of activity of the patient, etc.). If the monitored P-Q interval of the patient is less than the selected maximum P-Q threshold value, then the method 1300 may begin a process of delivering cardiac nerve stimulation 1306 to, e.g., treat potential heart failure, similar to the method 1200 described herein with reference to FIG. 14.

If the monitored P-Q interval of the patient is greater than selected maximum P-Q threshold value, then the patient may be undergoing symptoms indicative of unhealthy cardiac function. As a result, the method 1300 will deliver electrical pacing therapy 1310, e.g., premature nodal pacing. The electrical pacing therapy 1310 may include bradycardia pacing, cardiac resynchronization therapy, and/or other pacing therapies to modify the patient's heart rhythm for regulating preload and cardiac contractility to maintain healthy cardiac conditions.

Periodically and/or concurrently with electrical pacing therapy 1310, the method 100 may determine if the monitored P-Q interval of the patient is less than the selected minimum P-Q threshold value 1312. The selected minimum P-Q threshold value may be representative of the minimum P-Q interval indicative of improper preload and contractility of the heart, cardiac arrest, etc. For example, the selected minimum P-Q threshold value may be between about 180 ms to about 220 ms (e.g., depending on the cardiac health of the patient, the level of activity of the patient, etc.). If the P-Q intervals of the patient are less than the selected minimum P-Q threshold value, then the method 1300 may return to P-Q interval collection 1302.

If the monitored P-Q interval of the patient is greater than the selected minimum P-Q threshold value, then the method 1300 may continue delivering electrical pacing therapy 1310. Further, before, after, and/or during the electrical pacing therapy 1310, adjustment criteria may be evaluated 1314 and the electrical pacing therapy may be adjusted. Process 1314 may be similar to the processes 312 and 314 described herein with respect to FIG. 5 except, in this case, electrical pacing therapy as opposed to vagal stimulation may be adjusted. Further, the adjustment process 1314 may further include criteria based on ventricular pressure. Still further, process 1314 may further include various criteria, termination criteria, and/or clock criteria processes, which may includes processes similar to the processes 410, 414, and 416 described herein with respect to FIG. 6. In other words, method 1300 may switch between electrical stimulation to the patient's vagus nerve and electrical pacing therapy to the patient's heart based on the monitored electrical activity of the patient's heart.

If the monitored P-Q interval of the patient is greater than the selected minimum P-Q threshold value, then the method 1300 may continue delivering electrical pacing therapy 1310. Further, before, after, and/or during the electrical pacing therapy 1310, adjustment criteria may be evaluated 1314 and the electrical pacing therapy may be adjusted. Process 1314 may be similar to the processes 312 and 314 described herein with respect to FIG. 5 except, in this case, electrical pacing therapy as opposed to vagal stimulation may be adjusted. Further, the adjustment process 1314 may further include criteria based on ventricular pressure. Still further, process 1314 may further include various criteria, termination criteria, and/or clock criteria processes, which may be similar to the processes 410, 414, and 416 described herein with respect to FIG. 6.

In other words, method 1300 may switch between electrical stimulation to the patient's vagus nerve and electrical pacing therapy to the patient's heart based on the monitored electrical activity of the patient's heart and/or monitored ventricular pressure.

Further, situations may arise where vagal stimulation is being delivered to the heart of the patient for various reasons other than regulating preload and contractility. In these situations, cardiac pacing or nodal cardiac pacing may be delivered simultaneously with the vagal stimulation to attempt to shorten the P-R interval such that the vagal stimulation does not need to be adjusted (e.g., decreased).

In one or more embodiments described herein, vagal stimulation may also be delivered in response to premature ventricular beats, observed changes in parasympathetic/sympathetic balance (e.g., as derived from low frequency/high frequency ratio of the Fourier spectrum of HRV), TWA changes, HRT changes, baroflex changes as derived from pressure and HR, etc. In essence, such criteria may be a sub-threshold for delivering vagal stimulation before delaying the ventricular rate.

Still further, reentrant SVTs (e.g., AV nodal reentrant tachycardia, AV nodal tachycardia, etc.) may only require a brief AV block (e.g., one heart beat) for treatment. As such, vagal stimulation could be triggered upon detection of a reentrant SVT to cause a temporary AV block, which may lead to painless termination of the reentrant SVT.

Yet still further, the methods described herein may be used with or integrated with Medtronic Wavelet and/or EGM Width algorithms or other algorithms operable to compare intrinsic morphology and/or width of EGM for ventricular arrhythmia detection to, e.g., assess whether a "sure true" or "real" VT/VF.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:
1. A device for delivering cardiac therapy comprising:
monitoring apparatus configured to monitor physiological parameters of a patient's heart, wherein the monitoring apparatus comprises at least one electrode to monitor electrical activity of the patient's heart and at least one sensor to monitor pressure of a ventricle of the patient's heart;

a sensing module coupled to the monitoring apparatus and configured to receive the monitored physiological parameters;

a therapy delivery module configured to deliver electrical stimulation to the patient's vagus nerve; and a control module coupled to the sensing module and to the therapy delivery module and configured to:

monitor P-R intervals within the electrical activity of the patient's heart and ventricular pressure of the patient's heart prior to initiation of delivery of electrical stimulation to the patient's vagus nerve, and regulate preload and cardiac contractility of the patient's heart by initiating delivery of electrical stimulation to the patient's vagus nerve if a P-R interval monitored within the electrical activity of the patient's heart is less than a P-R interval threshold value and the monitored ventricular pressure of the patient's heart is greater than a pressure threshold value, wherein monitored P-R intervals less than the P-R interval threshold value are indicative of unhealthy preload and cardiac contractility, and wherein monitored ventricular pressures greater than pressure threshold value are indicative of unhealthy preload and cardiac contractility.

2. The device of claim 1, wherein the control module is further configured to control the delivery of electrical stimulation to the patient's vagus nerve to be synchronized to blanking periods associated with either of the P-waves or the R-waves within the electrical activity of the patient's heart.

3. The device of claim 1, wherein the control module is further configured to:

determine whether the patient's cardiac condition is worsening after the delivery of electrical stimulation to the patient's vagus nerve; and terminate the delivery of electrical stimulation to the patient's vagus nerve if the patient's cardiac condition is worsening.

4. The device of claim 3, wherein determining whether the patient's cardiac condition is worsening comprises determining whether the monitored physiological parameters of the patient indicate at least one of atrial fibrillation, ventricular arrhythmia, mechanical functional deterioration, and syncope, and wherein terminating the delivery of electrical stimulation to the patient's vagus nerve if the patient's cardiac condition is worsening comprises terminating the delivery of electrical stimulation to the patient's vagus nerve if the monitored physiological parameters of the patient indicate at least one of atrial fibrillation, ventricular arrhythmia, mechanical functional deterioration, and syncope.

5. The device of claim 1, wherein the therapy delivery module is further configured to deliver electrical pacing therapy to the patient's heart, and wherein the control module is further configured to initiate the delivery of electrical pacing therapy to the patient's heart if the electrical activity of the patient's heart is indicative of heart failure.

6. The device of claim 5, wherein the electrical activity of the patient's heart is indicative of heart failure if a P-R interval within the monitored electrical activity of the patient's heart is greater than a selected maximum P-R interval value.

7. The device of claim 5, wherein the control module is further configured to terminate the delivery of electrical pacing therapy to the patient's heart if a P-R interval within the monitored electrical activity of the patient's heart is less than a selected minimum P-R interval value.

8. A method for delivering cardiac therapy comprising:

monitoring P-R intervals within the electrical activity of a patient's heart prior to initiation of delivery of electrical stimulation to the patient's vagus nerve;

monitoring ventricular pressure of the patient's heart prior to initiation of delivery of electrical stimulation to the patient's vagus nerve; and regulating preload and cardiac contractility of the patient's heart by initiating delivery of electrical stimulation to the patient's vagus nerve if a P-R interval monitored within the electrical activity of the patient's heart is less than a P-R interval threshold value and the monitored ventricular pressure of the patient's heart is greater than a pressure threshold value, wherein monitored P-R intervals less than the P-R interval threshold value are indicative of unhealthy preload and cardiac contractility, and wherein monitored ventricular pressures greater than pressure threshold value are indicative of unhealthy preload and cardiac contractility.

9. The method of claim 8, wherein the delivery of electrical stimulation to the patient's vagus nerve is synchronized to blanking periods associated with either of the P-waves or the R-waves within the electrical activity of the patient's heart.

10. The method of claim 8, wherein the method further comprises:

determining whether the patient's cardiac condition is worsening after delivering electrical stimulation to the patient's vagus nerve, and terminating the delivery of electrical stimulation to the patient's vagus nerve if the patient's cardiac condition is worsening.

11. The method of claim 10, wherein determining whether the patient's cardiac condition is worsening comprises determining whether the monitored physiological parameters of the patient indicate at least one of atrial fibrillation, ventricular arrhythmia, mechanical functional deterioration, and syncope, and wherein terminating the delivery of electrical stimulation to the patient's vagus nerve if the patient's cardiac condition is worsening comprises terminating the delivery of electrical stimulation to the patient's vagus nerve if the monitored physiological parameters of the patient indicate at least one of atrial fibrillation, ventricular arrhythmia, mechanical functional deterioration, and syncope.

12. The method of claim 8, wherein the method further comprises delivering electrical pacing therapy to the patient's heart if the electrical activity of the patient's heart is indicative of heart failure.

13. The method of claim 12, wherein the electrical activity of the patient's heart is indicative of heart failure if a P-R interval within the monitored electrical activity of the patient's heart is greater than a selected maximum P-R interval value.

14. The method of claim 12, wherein the method further comprises terminating the delivery of electrical pacing therapy to the patient's heart if a P-R interval within the monitored electrical activity of the patient's heart is less than a selected minimum P-R interval value.

* * * * *